(12) United States Patent
Szeto et al.

(10) Patent No.: US 10,584,182 B2
(45) Date of Patent: *Mar. 10, 2020

(54) METHOD AND CARRIER COMPLEXES FOR DELIVERING MOLECULES TO CELLS

(71) Applicant: Cornell Research Foundation, Inc., New York, NY (US)

(72) Inventors: Hazel H. Szeto, New York, NY (US); Kesheng Zhao, Jackson Heights, NY (US); Hugh Robertson, New York, NY (US); Alex V. Birk, Woodhaven, NY (US)

(73) Assignee: Cornell Research Foundation, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/067,726

(22) Filed: Mar. 11, 2016

(65) Prior Publication Data
US 2017/0035899 A1 Feb. 9, 2017

Related U.S. Application Data

(63) Continuation of application No. 13/422,722, filed on Mar. 16, 2012, now Pat. No. 9,315,586, which is a continuation of application No. 12/631,048, filed on Dec. 4, 2009, now Pat. No. 8,148,322, which is a continuation of application No. 10/838,135, filed on May 3, 2004, now Pat. No. 7,704,954.

(60) Provisional application No. 60/467,516, filed on May 1, 2003.

(51) Int. Cl.
| | | |
|---|---|---|
| C07K 17/00 | (2006.01) |
| C07K 5/107 | (2006.01) |
| C07K 5/11 | (2006.01) |
| C12N 15/87 | (2006.01) |
| A61K 47/64 | (2017.01) |
| A61K 31/713 | (2006.01) |
| A61K 38/47 | (2006.01) |
| C12N 9/38 | (2006.01) |
| C12N 9/96 | (2006.01) |
| C12N 15/113 | (2010.01) |
| C07K 5/08 | (2006.01) |

(52) U.S. Cl.
CPC ............ *C07K 17/00* (2013.01); *A61K 31/713* (2013.01); *A61K 38/47* (2013.01); *A61K 47/64* (2017.08); *A61K 47/645* (2017.08); *C07K 5/08* (2013.01); *C07K 5/1016* (2013.01); *C07K 5/1019* (2013.01); *C12N 9/2471* (2013.01); *C12N 9/96* (2013.01); *C12N 15/113* (2013.01); *C12N 15/87* (2013.01); *C12Y 302/01023* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,312,899 A | 5/1994 | Schiller |
| 5,554,728 A * | 9/1996 | Basava ............... C07F 9/10 530/327 |
| 5,602,100 A | 2/1997 | Brown et al. |
| 5,652,122 A | 7/1997 | Frankel et al. |
| 5,674,534 A | 10/1997 | Zale et al. |
| 5,716,644 A | 2/1998 | Zale et al. |
| 5,747,026 A | 5/1998 | Crapo et al. |
| 5,885,958 A | 3/1999 | Zadina et al. |
| 5,993,848 A | 11/1999 | Suzuki et al. |
| 5,994,372 A | 11/1999 | Yaksh |
| 6,221,355 B1 | 4/2001 | Dowdy |
| 6,268,398 B1 | 7/2001 | Ghosh et al. |
| 6,468,798 B1 | 10/2002 | Debs et al. |
| 6,503,713 B1 | 1/2003 | Rana |
| 6,703,483 B1 | 3/2004 | Schiller |
| 6,759,520 B1 | 7/2004 | Carr et al. |
| 6,900,178 B2 | 5/2005 | Oeltgen et al. |
| 7,498,297 B2 | 3/2009 | Szeto et al. |
| 2003/0198595 A1 | 10/2003 | Goldenberg et al. |
| 2004/0029796 A1 | 2/2004 | Szeto et al. |
| 2004/0248808 A1 | 12/2004 | Szeto et al. |
| 2005/0096333 A1 | 5/2005 | Dugar et al. |

(Continued)

FOREIGN PATENT DOCUMENTS

| | | |
|---|---|---|
| CA | 20002361364 | 9/2000 |
| EP | 2 491 943 A2 | 8/2012 |

(Continued)

OTHER PUBLICATIONS

Shimoyama et al. ("Anticociceptive and Respiratory Effects of Intrathecal H-Tyr-D-Arg-Phe-Lys-NH2 (Dalda) and Dmt1-Dalda" The Journal of Pharmcology and Experimental Therapeutics; 2001).*
Lambert ("Rationale and applications of lipids and prodrug carriers" European Journal of Pharmaceutical Sciences 11 Suppl. 2 (2000) S15-S27).*
Marcey (Bonding and Protein Structure, 2001).*
Stevens et al. ("Routes of Opiod Analgesic Therapy in the Management of Cancer Pain" Cancer Control; Mar./Apr. 2000 vol. 7, No. 2).*

(Continued)

*Primary Examiner* — James H Alstrum-Acevedo
*Assistant Examiner* — Tara L Martinez
(74) *Attorney, Agent, or Firm* — Foley & Lardner LLP

(57) ABSTRACT

The invention relates to carrier complexes and methods for delivering molecules to cells. The carrier complexes comprises a molecule and an aromatic cationic peptide in accordance with the invention. In one embodiment, the method for delivering a molecule to a cell comprises contacting the cell with a carrier complex. In another embodiment, the method for delivering a molecule to a cell comprises contacting the cell with a molecule and an aromatic cationic peptide.

12 Claims, 17 Drawing Sheets

Specification includes a Sequence Listing.

(56) References Cited

U.S. PATENT DOCUMENTS

| | | |
|---|---|---|
| 2005/0158373 A1 | 7/2005 | Szeto et al. |
| 2005/0192215 A1 | 9/2005 | Ghosh et al. |
| 2006/0084606 A1 | 4/2006 | Szeto |
| 2007/0015711 A1 | 1/2007 | Szeto |
| 2007/0027070 A1 | 2/2007 | Szeto et al. |
| 2007/0027087 A1 | 2/2007 | Szeto et al. |
| 2007/0093969 A1 | 4/2007 | Mendrick et al. |
| 2007/0129306 A1 | 6/2007 | Szeto et al. |
| 2007/0259377 A1 | 11/2007 | Urdea et al. |
| 2008/0014604 A1 | 1/2008 | Devarajan et al. |
| 2008/0027082 A1 | 1/2008 | Hocher et al. |
| 2009/0221514 A1 | 9/2009 | Szeto et al. |
| 2009/0253641 A1 | 10/2009 | Neufer et al. |
| 2009/0264369 A1 | 10/2009 | Szeto et al. |

FOREIGN PATENT DOCUMENTS

| | | |
|---|---|---|
| JP | 2007-503461 | 2/2007 |
| WO | WO-79/00515 | 8/1979 |
| WO | WO-91/18012 A1 | 11/1991 |
| WO | WO-95/22557 | 8/1995 |
| WO | WO-96/40073 | 12/1996 |
| WO | WO-99/15154 | 4/1999 |
| WO | WO-00/38651 | 7/2000 |
| WO | WO-00/55189 | 9/2000 |
| WO | WO-01/66147 A2 | 9/2001 |
| WO | WO-02/05748 A2 | 1/2002 |
| WO | WO-02/36612 | 5/2002 |
| WO | WO-02/065986 | 8/2002 |
| WO | WO-02/069930 | 9/2002 |
| WO | WO-02/089776 | 11/2002 |
| WO | WO-2004/070054 A2 | 8/2004 |
| WO | WO-2005/001023 | 1/2005 |
| WO | WO-2005/072295 A2 | 8/2005 |
| WO | WO-2007/035640 A2 | 3/2007 |

OTHER PUBLICATIONS

Prozyme (Alternative conjugation Protocols; Feb. 1, 2001).*
Extended Search Report issued on European Application 16188609.8, dated Apr. 12, 2017.
Office Action issued on Japanese Application 2016-050272, dated Mar. 13, 2017.
Rigaudy et al., "Synthesis and binding properties to DNA and to opioid receptors of encephalin-ellipticinium conjugates," Int. J. Peptide Protein Res., vol. 30, 1987, pp. 347-355.
Aitman, et al.; "Identification of CD36 (Fat) as an insulin resistance gene causing defective fatty acid and glucose metabolism in hypertensive rats"; Nature Genetics (Jan. 1999); vol. 21, pp. 76-83.
Alam, N.M. et al., "A Novel Peptide (MTP-131) that Improves Mitochondrial Function Reverses Visual Decline in Mouse Models of Metabolic Dysfunction Leading to Diabetes," American Diabetes Association, (2012), Poster Presentation (1 page).
Alam, N.M. et al., "Reducing Mitochondrial Oxidative Stress to Treat Diabetes and Age-related Visual Decline," Society of Neuroscience, (2011), Poster Presentation (1 page).
Alam, Nazia et al., "A novel Peptide that Improves Mitochondrial Function Reverses Diabetes- and Age-Related Visual Decline," American Aging Association, (2012), Abstract (1 page).
Anderson, Ethan J. et al., "Mitochondrial H2O2 emission and cellular redox state link excess fat intake to insulin resistance in both rodents and humans," J. Clin. Invest., (Feb. 2009), vol. 119, No. 3, pp. 573-581.
Andersson, Daniel C. et al., "Mitochondrial production of reactive oxygen species contributes to the β-adrenergic stimulation of mouse cardiomycytes," J. Physiol., (2011), 589(7), pp. 1791-1801.
Azzouz, "Gene therapy for ALS: progress and prospects," Biochimical et Biophysica Acta, 1762:1122-1127, 2006.
Berendsen, "A glimpse of the holy grail?" Science, 282:642-643, 1998.
Bickel et al., Synthesis and bioactivity of monobiotinylated DALDA: A Mu-specific opioid peptide designed for targeted brain delivery, J Pharmacol and Exp Therapeutics, 268(2): 791-796 (1994).

Bork et al., "Go hunting in sequence databases but watch out for the traps," Trends in Genetics, 12:425-427, 1996.
Bork, "Powers and pitfalls in sequence analysis: the 70% hurdle," Genome Research, 10:398-400, 2000.
Borrell-Pages et al., "Cystamine and cysteamine increase brain levels of BDNF in Huntington disease via HSJ1b and transgulataminase"; Journal of Clinical Investigation; May 2006; vol. 116, No. 5, pp. 1410-1424.
Bradley et al., "Limits of cooperativity in a structurally modular protein: response of the notch ankyrin domain to analogous alanine substitutions in each repeat," J. Mol. Biol., 324:373-386, 2002.
Brazilian Official Communication with translation issued by Ministry of Development, Industry and Foreign Trade National Institute of Industrial Property Presidency received in Brazilian Patent Appln. No. PI0409911-7 on Mar. 12, 2012.
Brenner, "Errors in genome annotation," Trends in Genetics, 15:132-133, 1999.
Broekemeier et al., "Inhibition of the mitochondrial permeability transition by Cyclosporin A during long time frame experiments: Relationship between pore opening and the activity of mitochondrial phospholipases," Biochemistry, 34:16440-16449, 1995.
Brown, David A. et al., "Bendavia, a mitochondria-targeting peptide, reduces reperfusion injury and reactive oxygen species levels through a mechanism independent of direct oxygen radical scavenging: A multicenter study," American Heart Association, (2012), Abstract (1 page).
Brown, David A., Ph.D., "Mitochondrial Derived Cardioprotection in Exercised Hearts: Role of Cardiac Glutathione," American College of Sports Medicine, (2012), DB Lab Presentation (28 pages).
Calkins, Marcus J. et al., "Impaired mitochondrial biogenesis, defective axonal transport of mitochondria, abnormal mitochondrial dynamics and synaptic degeneration in a mouse model of Alzheimer's disease," Hum. Mol. Genet., (2011), vol. 20, No. 23, pp. 4515-4529.
Cao, Mingfeng et al., "Mitochondria-targeted antioxidant attenuates high glucose-induced P38 MAPK pathway activation in human neuroblastoma cells," Mol. Med. Report., (2012), 5(4), pp. 929-934.
Carter, Edward A. et al., "Evaluation of the antioxidant peptide SS31 for treatment of burn-induced insulin resistance," Int. J. Mol. Med., (2011), 28(4), pp. 589-594.
Chen, Min et al., "Mitochondria-targeted Peptide MTP-131 Alleviates Mitochondrial Dysfunction and Oxidative Damage in Human Trabecular Meshwork Cells," Invest. Ophthalmol. & Vis. Sci., (Sep. 2011), vol. 52, No. 10, pp. 7027-7037.
Cho, Janghyun et al., "Potent mitochondria-targeted peptides reduce myocardial infarction in rats," Coron. Artery Dis., (2007), vol. 18, No. 3, pp. 215-220.
Cho, Sunghee et al., "A Novel Cell-permeable Antioxidant Peptide, SS31, Attenuates Ischemic Brain Injury by Down-regulating CD36," J. Biol. Chem., (Feb. 2007), vol. 282, No. 7, pp. 4634-4642.
Chonn, Arcadio et al., "Recent Advances in Liposomal Drug-Delivery Systems," Current Opinion in Biotechnology, (1995), vol. 6, pp. 698-708.
Citron, "Alzheimer's Disease: Treatments in discovery and development," Nature Neuroscience Supplement, 5:1055-1057, 2002.
Clapp III et al., "Cardiovascular and metabolic responses to two receptor-selective opioid agonists in pregnant sheep," Am J Obstet Gynec., 178(2):397-401, 1998.
Corpeleijn, et al.; "Direct association of a promoter polymorphism in the CD36/FAT fatty acid transporter gene with Type 2 diabetes mellitus and insulin resistance"; Diabetic Medicine (2006); vol. 23, pp. 907-911.
Dai, Dao-Fu et al., "Mitochondrial targeted antioxidant peptide ameliorates hypertensive cardiomyopathy," J. Am. Coll. Cardiol., (2011), vol. 58, No. 1, pp. 73-82.
Demas, et al., "Anaesthesia for Heart Transplantation," Br J. Anaesth., (1986) vol. 58, pp. 1357-1364.
Dimaio et al., "Synthesis and pharmacological characterization in vitro of cyclic enkephalin analogues, Effect of Conformational Constraints on Opiate Receptor Selectivity," J. Med. Chem., 25:1432-1438, 1982.
Doerks et al., "Protein annotation: detective work for function prediction," Trends in Genetics, 14(6):248-250, 1998.

(56) References Cited

OTHER PUBLICATIONS

Dooley, et al., "Selective ligands for the mu, delta and kappa opioid receptors identified from a single mixture based tetrapeptide positional scanning combinatorial library," Journal of Biological Chemistry, 273(30):18848-18856, 1998.
Drin et al., "Studies on the internationalization mechanism of cationic cell-penetrating peptides," Journal of Biological Chemistry, vol. 278, No. 33, pp. 31192-31201 (2003).
Eirin, Alfonso et al., "A Mitochondrial Permeability Transition Pore Inhibitor Improves Renal Outcomes After Revascularization in Experimental Atherosclerotic Renal Artery Stenosis," J. Am. Heart Assoc., (2012), vol. 60, pp. 1242-1249; available at http://hyper.ahajournals.org/content/60/5/1242 and supplemental content available at http://hyper.ahajournals.org/content/suppl.2012/10/08/HYPERTENSIONAHA.112.199919.DC1.html (26 pages total).
Eirin, Alfonso et. al., "Chronic Treatment with Bendavia Preserves the Stenotic Kidney in Swine Atherosclerotic Renovascular Disease (ARVD)," American Society of Nephrology, (2012), Abstract & figures (2 pages).
Eirin, Alfonso et. al., "Mitochondrial Targeted Peptides Attenuate Myocardial Damage after Renal Revascularization in Experimental Atherosclerotic Renovascular Hypertension," American Society of Nephrology, (2012), Abstract & figures (2 pages).
Eirin, Alfonso, et. al., "MTP-131 reduces renal injury after percutaneous transluminal renal angioplasty (PTRA) in swine atherosclerotic renal artery stenosis (ARAS)," American Society of Nephrology, (2011), Poster Presentation (1 page).
English translation of Office Action on Japanese Application No. 2011-087496 dated Mar. 10, 2014, 2 pages.
EPO Communication pursuant to Article 94(3) EPC, Examination Report on Application 04751253.8 dated May 14, 2013, (9 pages).
EPO Communication pursuant to Article 94(3) EPC, Examination Report on Application No. 04751253.8 dated Oct. 8, 2014 (4 pages).
Examiner's first report in Australian Patent Application 2004252419, dated Nov. 27, 2009.
Final Office Action received for U.S. Appl. No. 10/838,135 dated May 27, 2009.
Fuhrman, et al., "Oxidative stress increases the expression of the CD36 scavenger receptor and the cellular uptake of oxidized low-density lipoprotein in macrophages from atherosclerotic mice: protective role of antioxidants and of paraoxonase," Atherosclerosis, (2002), 161, pp. 307-316.
Gilliam, Laura A.A. et al., "Doxorubicin acts via mitochondrial ROS to stimulate catabolism in C2C12 myotubes," Am. J. Physiol. Cell Physiol., (Sep. 2011), 302(1), pp. C195-C202.
Gregoriadis, "Engineering Liposomes for Drug Delivery: Progress and Problems," TIBTECH, (1995), vol. 13, pp. 527-537 (11 pages).
Guerrini et al., Opioid receptor selectivity alteration by single residue replacement: synthesis and activity profile of [Dmt] deltorphin B, European Journal of Pharmacology, 302:37-42, 1996 (abstract only.).
Hale, Sharon L. et. al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, (2011), Poster Presentation (1 page).
Han, Zhaosheng et al., "Mitochondria-Derived Reactive Oxygen Species Mediate Heme Oxygenase-1 Expression in Sheared Endothelial Cells"; J. Pharmacol. Exp. Ther., (2009), vol. 329, No. 1, pp. 94-101.
Herve et al., "On the immunogenic properties of retro-inverso peptides. Total retro-inversion of t-cell epitopes causes a loss of binding to MHC II molecules," Molecular Immunology, 34(2):157-163, 1997.
Holsey et al., "Cardiovascular effects of a µ-selective opioid agonist (Tyrosine-D-Arginine-Phenylalanine-Lysine-NH2) in fetal sheep; Sites and Mechanisms of Action," Am. J. Obstet. Gynecol., 180(5):1127-1130, 1999.
International Search Report in International Application No. PCT/US2004/013772, dated Jan. 31, 2005.

Janaky et al., "Analogues of luteinizing hormone-releasing hormone containing cytotoxic groups," Proc. Natl. Acad. Sci. USA, 1992, vol. 89, No. 3, pp. 972-976.
Janaky et al., "Short-chain analogs of luteinizing hormone-releasing hormone containing cytotoxic moieties," Proc. Natl. Acad. Sci. USA, 1992, vol. 89, No. 21, pp. 10203-10207.
Japanese Office Action with English translation dated Mar. 18, 2013, regarding Japanese Patent Appln. No. 2011-087496,(2 pages).
Kett et al., "Baroreflex-mediated bradycardia but not tachycardia is blunted peripherally by intravenous µ-opioid agonists," Am. J. Obstet. Gynecol., 178(5):950-955, 1998.
Kloner, Robert A. et al., "Reduction of Ischemia/Reperfusion Injury with Bendavia, a Mitochondria-Targeting Cytoprotective Peptide," J. Am. Heart Assoc., vol. 1, (2012), available at http://jaha.ahajournals.org/content/1/3/e001644 (14 pages).
Kloner, Robert A., et. al., "Bendavia, a Novel Mitochondrial-Targeted Cytoprotective Compound Reduces Ischemia/Reperfusion Injury: Experience in 3 Independent Laboratories," American Heart Association, (2011), Abstract (2 pages).
Korczyn et al., "Emerging therapies in the pharmacological treatment of Parkinson's Disease," Drugs, 62(5):775-786, 2002.
Langedijk, et al., "Translocation Activity of C-terminal Domain of Pestivirus Erns and Ribotoxin L3 Loop", (2002), Journal of Biological Chemistry, vol. 277, No. 7, pp. 5308-5314.
Lasukova et al., "Activation of mu-opioid receptors and cardiomyocyte resistance to free radical damage," Patol Fiziol Eksp Ter., 2:15-17, English Abstract Only, 2001.
Lee, Hyung-yul et al., "Novel Mitochondria-Targeted Antioxidant Peptide Ameliorates Burn-Induced Apoptosis and Endoplasmic Reticulum Stress in the Skeletal Muscle of Mice," Shock, (2011), vol. 36, No. 6, pp. 580-585.
Li, Jianqiao et al., "Mitochondria-targeted antioxidant peptide SS31 attenuates high glucose-induced injury on human retinal endothelial cells," Biochem. & Biophys. Res. Commun., (2011), 404, pp. 349-356.
Liang, XL., et. al., "SS31 protects human RPE cells from oxidative damage and reduces laser-induced choroidal neovascularization," Association for Research in Vision and Opthamology, (2010), Poster Presentation (1 page).
Lichtenberg, D. et al., "Liposomes: Preparation, Characterization and Preservation," Methods of Biochemical Analysis, (1988), vol. 33, pp. 337-462 (128 pages).
Lishmanov et al., "Ligands for opioid and o-receptors improve cardiac electrical stability in rat models of post-infarction cardiosclerosis and stress," Life Sciences, 65:13-17, 1999.
Liu, Shaoyi et. al., "Boosting mitochondrial function to minimize ischemia-reperfusion injury," Experimental Biology, (2011), Poster Presentation (1 page).
Liu, Shaoyi et. al., "Mitochondria-targeting peptide (SS-31) promotes rapid repair of actin cytoskeleton following ischemia and protects tubular epithelial cell architecture," American Society of Nephrology, (2012), Abstract (2), (1 page).
Ma, Qi et al., "Superoxide Flashes: Early Mitochondrial Signals for Oxidative Stress-Induced Apoptosis," J. Biol. Chem., (Aug. 2011), vol. 286, No. 31, pp. 27573-27581.
Majer et al., "Synthesis of methylated phenylalanines via hydrogenolysis of corresponding 1,2,3,4-tetrahydroisoquinoline-3-caraboxylic acids," Int. J. Peptide Protein Res., 43:62-68, 1994.
Manczak, Maria et al., "Mitochondria-Targeted Antioxidants Protect Against Amyloid-β toxicity in Alzheimer's Disease Neurons," J. Alzheimer's Dis., (2010), 20, pp. S609-S631.
Marcinek, David J., et al., "Acute pharmacological intervention reverses mitochondrial deficits and improves function in aged skeletal muscle," American Aging Association, (2012), Abstract (1 page).
Margolis et al., "Diagnosis of Huntington Disease," Clinical Chemistry, 49(10):1726-1732, 2003.
Min, Kisuk et al., "Mitochondrial-targeted antioxidants attenuate immobilization-induced skeletal muscle atrophy," Experimental Biology Meeting 2010, Anaheim CA, USA, Apr. 24-28, 2010, FASEB Journal, (2010) vol. 24: Abstract 1b670, (1 page).

(56) References Cited

OTHER PUBLICATIONS

Min, Kisuk et al., "Mitochondrial-targeted antioxidants protect skeletal muscle against immobilization-induced muscle atrophy," J. Appl. Physiol., (2011), 111(5), pp. 1459-1466.
Mizuguchi, Yasunori et al., "A novel cell-permeable antioxidant peptide decreases renal tubular apoptosis and damage in unilateral ureteral obstruction," Am. J. Physiol. Renal Physiol., (2008), 295, pp. F1545-F1553.
Moosmann, et al.; "Secretory Peptide Hormones are Biochemical Antioxidants: Structure-Activity Relationship"; Mol. Pharmacol. (2002); vol. 61(2), pp. 260-268.
Neilan, et al., "Pharmacological characterization of the dermorphin analog [Dmt(1)]DALDA, a highly potent and selective mu-opioid peptide", European Journal of Pharmacology, (2001), vol. 419, No. 1, pp. 15-23.
Ngo et al., "Computational complexity, protein structure prediction, and the leventhal paradox," The protein folding problem and tertiory structure prediction, (Ed. K. Mertz Jr. and S. Le Grand), Birkhauser Boston, 492-495, 1994.
Nieborowska-Skorska, Margaret et al., "Rac2-MRC-clll-generated ROS cause genomic instability in chronic myeloid leukemia stem cells and primitive progenitors," Blood, (2012), vol. 119, No. 18, pp. 4253-4263.
Non-final Office Action received for U.S. Appl. No. 10/838,135 dated Dec. 24, 2008.
Non-Final Office Action received for U.S. Appl. No. 12/631,048 dated Jun. 24, 2012.
Notice of Allowance received for U.S. Appl. No. 13/422,722 dated Dec. 14, 2015, 31 pages.
Notice of Allowance with English Translation received in Korean Patent Appln. No. 10-2005-7020664 dated Apr. 3, 2012.
Notice of Reason for Rejection with English Translation received in Korean Patent Appln. No. 2005-7020664, dated Nov. 30, 2010, 3 pages.
Notice of the Reason for Rejection issued by the Korean Intellectual Property Office in Appln. No. 2005-7020664 dated Aug. 9, 2011 1 page.
Notice of the Reasons for Rejection issued by the Korean Intellectual Property Office received in Korean Appln. No. 2005-7020664 dated Aug. 9, 2011, 1 page.
Notification of the First Office Action issued by the State Intellectual Property Office of P.R.C. received in Chinese Appln. No. 200810000182.7 dated Feb. 12, 2010, 4 pages.
Official Communication issued by the European Patent Office dated Mar. 7, 2011; 12 pages.
Omoniyi et al., "A peripheral site of action for the attenuation of baroreflex-mediated bradycardia by intravenous μ-opioid agonists," Journal of Cardiovascular Pharmocolgy, 35(2):269-274, 2000.
Park, et al., "ATTEMPTS: a heparin/protamine-based triggered release system for the delivery of enzyme drugs without associated side-effects", (2003), Advanced Drug Delivery Reviews, vol. 55, pp. 251-265.
Patel et al., "Pharmacotherapy of cognitive impairment in Alzheimer's Disease: A Review," J. Geriatr. Psychiatry Neurol., 8:81-95, 1995.
Petri, Susanne et al., "Cell-permeable peptide antioxidants as a novel therapeutic approach in a mouse model of amyotrophic lateral sclerosis", Journal of Neurochemistry, (2006), vol. 98, pp. 1141-1148.
Powers, Scott K. et al., "Mitochondria-targeted antioxidants protect against mechanical-ventilation-induced diaphragm weakness," Crit. Care Med., (2011), vol. 39, No. 7, pp. 1749-1759.
Putney, S.D., "Encapsulation of proteins for improved delivery," Current Opinion in Chemical Biology, (1998), vol. 2, No. 4, pp. 548-552.
Rabinovitch, Peter, "Mitochondrial Oxidative Stress and Cardiac Aging," Basic Cardiovascular Sciences, (2011), Presentation (19 pages).
Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Reddy, P. Hemachandra, "Amyloid beta Toxicity, Mitochondrial Dysfunction and Synaptic Damage in Alzheimer's Disease: Implications for Mitochondria-Targeted Antioxidant Therapeutics," New York Academy of Sciences, (2010), Abstract (1 page).
Reddy, Tejaswini P. et al., "Toxicity of Neurons Treated with Herbicides and Neuroprotection by Mitochondria-Targeted Antioxidant SS31," Int. J. Environ. Res. & Public Health, (2011), 8, pp. 203-221.
Rudinger, "Characteristics of the amino acids as components of a peptide hormone sequence," Peptide Hormones, Ed. J. A. Parson, University Park Press, Baltimore, pp. 1-7, 1976.
Sabbah, Hani N. et al., "Acute Intravenous Infusion of Bendavia (MTP-131), a Novel Mitochondria-Targeting Peptide, Improves Left Ventricular Systolic Function in Dogs With Advanced Heart Failure," American Heart Association, (2012), Abstract (1 page).
Schiller et al., "Dermorphin analogues carrying an increased positive net charge in their "message" domain display extremely high μ-opioid receptor selectivity," J. Med. Chem., 32(3):698-703, 1989.
Schiller et al., "Opioid peptide analogs with novel activity profiles as potential therapeutic agents for use in analgesia," Peptide Science-Present and Future, Proc. 1st Int. Pept. Symp., 665-669, 1999.
Schiller et al., "Synthesis and in vitro opioid activity profiles of DALDA analogues," European Journal of Medicinal Chemistry, 35(10):895-901, 2000.
Schiller et al., "Tipp: A highly potent and stable pseudopeptide opioid receptor antagonist with extraordinary selectivity," J. Med. Chem., 36:3182-3187, 1993.
Schiller et al., "Unsulfated C-terminal 7-peptide of cholecystokinin: a new ligand of the opiate receptor," Biochemical and Biophysical Research Communications, 85(4):1332-1338, 1978.
Schwarze, et al., "In vivo protein transduction: delivery of a biologically active protein into a mouse", (1999), vol. 285, No. 5433, pp. 1569-1572.
Schwarze, et al., "In vivo protein transduction: intracellular delivery of biologically active proteins, compounds and DNA," Trends in Pharmacological Sciences, 21(2):45-48, 2000.
Search Report on European Application No. 13159237.0 dated May 2, 2013, 7 pages.
Search Report on European Application No. 13159248.7 dated Mar. 14, 2014, 8 pages.
Shahrzad, et al., "Impact of water-dispersible beadlets as a vehicle for the delivery of carotenoids to cultured cells", (2002), BioFactors, vol. 16, pp. 83-91.
Sharma, Lokendra Kumar et al., "Mitochondrial respiratory complex I dysfunction promotes tumorigenesis through ROS alteration and AKT activation," Hum. Mol. Genet., (2011), vol. 20, No. 23, pp. 4605-4616.
Shimoyama, et al., "Antinociceptive and Respiratory Effects of Intrathecal H-Tyr-D-Arg-Phe-Lys-NH2 (DALDA) and [Dmt1] DALDA", Journal of Pharmacology and Experimental Therapeutics, (2001), vol. 297, No. 1, pp. 364-371.
Shroff, et al., "Effects of intrathecal opioid on extubation time, analgesia and intensive care unit stay following coronary artery bypass grafting," Journal of Clinical Anesthesia, 9:415-419, 1997.
Simmons,Zachary, "Management strategies for patients with Amyotrophic Lateral Sclerosis from diagnosis through death," The Neurologist, abstract only (File Medline on STN. An No. 2005478947), 11(5):257-270, 2005.
Skolnick et al., "From genes to protein structure and function: novel applications of computational approaches in the genomic era," Trends in Biotech, 18(1):34-39, 2000.
Sloan, Ruben C. et al., "Mitochondrial permeability transition in the diabetic heart: Contributions of thiol redox state and mitochondrial calcium to augmented reperfusion injury," J. Mol. Cell. Cardiol., (2012), 52, pp. 1009-1018.
Smith et al., "The challenges of genome sequence annotation or The devil is in the details," Nature Biotechnology, 15:1222-1223, 1997.
Song et al., "A Potent Opiate Agonist Protects Against Myocardial Stunning During Myocardial Ischemia and Reperfusion in Rats," Coronary Artery Disease, 16(6):407-410, 2005.

(56) References Cited

OTHER PUBLICATIONS

Spetea, et al., "Interaction of agonist peptides [3H]Tyr-D-Ala-Phe-Phe-NH2 with mu-opioid receptor in rat brain and CHO-mu/1 cell line," Peptides, 19(6):1091-1098, 1998.
Sriram et al., "Experimental allergic encephalomyelitis: A Misleading Model of Multiple Sclerosis," Ann. Neurol., 58:939-945, 2005.
Steinman et al., "How to successfully apply animal studies in experimental allergic encephalomyelitis to research on multiple dclerosis", Annals of Neurology, 2006, vol., pp. 12-21.
Szeto et al., "Mu-opioid receptor densensitization and resensitization in vivo," International Narcotics Research Conference, Poster Abstracts, Monday, Mon19:5, 1999.
Szeto, "Development of Mitochondria-targeted Aromatic-cationic Peptides for Neurodegenerative Diseases," Ann. N.Y. Acad. Sci., (2008), 1147, pp. 112-121.
Szeto, et al., "In Vivo Disposition of Dermorphin Analog (DALDA) in Nonpregnant and Pregnant Sheep1," The Journal of Pharmacology and Experimental Therapeutics, (1998), 284(1), pp. 61-65.
Szeto, et al., "In vivo Pharmacokinetics of Selective µ-Opioid Peptide Agonists," The Journal of Pharmacology and Experimental Therapeutics, (2001), 298(1), pp. 57-61.
Szeto, et al., "Novel Therapies Targeting Inner Mitochondrial Membrane—from Discovery to Clinical Development", Pharm. Res., (2011), vol. 28, pp. 2669-2679.
Szeto, et al., "Respiratory depression after intravenous administration of d-selective opioid peptide analogs," Peptides, (1999), 20, pp. 101-105.
Szeto, Hazel H. "Mitochondria-targeted peptide antioxidants: Novel Neuroprotective Agents," The AAPS Journal, (2006), 8(3), Article 62, pp. E521-E531.
Szeto, Hazel H. et al., "Mitochondria-Targeted Peptide Accelerates ATP Recovery and Reduces Ischemic Kidney Injury," J. Am. Soc. Nephrol., (2011), 22, pp. 1041-1052.
Szeto, Hazel H. et. al., "Mitochondria-targeting peptide (SS-31, Bendavia®) prevents microvascular rarafaction, inflammation, and fibrosis caused by ischemia-reperfusion injury," American Society of Nephrology, (2012), Abstract (1 page).
Szeto, Hazel H., "Cell-permeable, Mitochondrial-targeted, Peptide Antioxidants," The AAPS Journal, (2006), 8(2) Article 32, pp. E277-E283.
Szeto, Hazel H., "Mitochondrial Protection as Strategy to treat Ischemia-Reperfusion Injury," American Society of Nephrology, (2010), Presentation (17 pages).
Szeto, Hazel H., "The development of a therapeutic peptide for mitochondrial protection—from bench to bedside," Experimental Biology, (2011), Poster Presentation (1 page).
Szeto, Hazel H., "Mitochondria-Targeted Cytoprotective Peptides for Ischemia-Reperfusion Injury," Antioxid. Redox Signal, (2008), vol. 10, No. 3, pp. 601-619.
Szeto, Hazel H., et. al., "Rapid Restoration of ATP by SS-31, an Inhibitor of Mitochondrial Permeability Transition, Prevents Tubular Cytoskeletal Rearrangement in Renal Ischemia-Reperfusion Injury," American Society of Nephrology, (2010), Poster Presentation (1 page).
Thomas, et al., "Mitochondrial Targeting with Antioxidant Peptide SS-31 Prevents Mitochondrial Depolarization, Reduces Islet Cell Apoptosis, Increases Islet Cell Yield, and Improves Posttransplantation Function," J. Am. Soc. Nephrol. 18:213-222 (2007).
Tiganis, Tony, "Reactive Oxygen Species & NAPDH Oxidases in Insulin Signalling," NOX Gordon Research Conference, (Jun. 3-8, 2012), Presentation (44 pages).
Traber, et al., "Uptake of intact TPGS (d-alpha-tocopheryl polyethylene glycol 1000 succinate) a water-miscible form of vitamin E by human cells in vitro", (1988), American Journal of Clinical Nutrition, vol. 48, pp. 605-611.
Unger, et al., "Hyperglycaemia as an inducer as well as a consequence of impaired islet cell function and insulin resistance: implications for the management of diabetes," Diabetologia, (1985), vol. 28, No. 3, pp. 119-121.

U.S. Notice of Allowance received for U.S. Appl. No. 10/838,135 dated Sep. 2, 2009.
U.S. Notice of Allowance received for U.S. Appl. No. 12/631,048 dated Nov. 28, 2011.
U.S. Office Action dated Mar. 27, 2013.
Vaara M et al., "Group of peptides that act synergistically with hydrophobic antibiotics against gram-negative enteric bacteria", Antimicrob Agents Chemother vol. 40, No. 8: 1801-1805 (1996).
Villaverde, et al., "A Cell Adhesion Peptide from Foot-and-Mouth Disease Virus Can Direct Cell Targeted Delivery of a Functional Enzyme", (1998), Biotechnology and Bioengineering, vol. 59, No. 3, pp. 294-301.
Wang, Dantong et al., "Elevated Mitochondrial Reactive Oxygen Species Generation Affects the Immune Response via Hypoxia-Inducible Factor-1α in Long-Lived Mclk1+/− Mouse Mutants," J. Immunol., (2010), 184(2), pp. 582-590.
Weiner, Alan L., "Liposomes for Protein Delivery: Selecting Manufacture and Development Processes," Immunomethods, (1994), 4(3), pp. 201-209.
Wells, "Additivity of Mutational Effects in Proteins," Biochemistry, American Chemical Society, (1990), 29(37), pp. 8509-8517.
Whiteman, Matthew et al., "Do Mitochondriotropic Antioxidants Prevent Chlorinative Stress-Induced Mitochondrial and Cellular Injury?" Antioxid. Redox Signal., (2008), vol. 10, No. 3, pp. 641-650.
Wu et al., "Myocardial protective effect of mu opioid agonists," International Narcotics Research Conference, Poster Abstracts, Sun 59:15, 1999.
Wu, et al., "A highly potent peptide analgesic that protects against ischemia-reperfusion-induced myocardial stunning", American Journal of Physiology Heart and Circulatory Physiology, (2002), vol. 283, pp. H783-H791.
Yang, Lichuan et al., "Mitochondria Targeted Peptides Protect against 1-Methyl-4-Phenyl-1,2,3,6-Tetrahydropyridine Neurotoxicity," Antioxid Redox Signal., (2009), vol. 11, No. 9, pp. 2095-2104.
Zadina, et al., "A potent and selective endogenous agonist for the mu-opiate receptor," Nature, 386:499-502, 1997.
Zhao et al., "Cell-permeable peptide antioxidants targeted to inner mitochondrial membrane inhibit mitochondrial swelling, oxidative cell death, and reperfusion injury," J. Biol. Chem., (2004), vol. 279, No. 33, pp. 34682-34690.
Zhao, et al., "Profound spinal tolerance after repeated exposure to a highly selective u-opioid peptide agonist: Role of o-opioid receptors," J Pharma. Exper. Thera., 302(1):188-196, 2002.
Zhao, et al., "Translocation of a 3+ net charge tetrapeptide across plasma membrane of mammalian cells," Abstract published on-line May 1, 2002, World Congress of Pharmacology Meeting, held Jul. 2002.
Zhao, Guo-Min et al., "Comparison of [Dmt1]DALDA and DAMGO in Binding and G Protein Activation at µ, δ, and κ Opioid Receptors," J. Parmacology and Experimental Therapeutics, (2003), vol. 307, No. 3, pp. 947-954.
Zhao, Kesheng et al., "Transcellular Transport of a Highly Polar 3+ Net Charge Opioid Tetrapeptide," Journal of Pharmacology and Experimental Therapeutics, (2003), vol. 304, No. 1, pp. 425-432.
Zhao, Kesheng et al., "Mitochondria-targeted peptide prevents mitochondrial depolarization and apoptosis induced by tert-butyl hydroperoxide in neuronal cell lines," Biochem. Pharmacol., (2005), 70, pp. 1796-1806.
Zhu, Huaqing et al., "Histone Deacetylase-3 Activation Promotes Tumor Necrosis Factor-α(TNF-α) Expression in Cardiomyocytes during Lipopolysaccharide Stimulation," J. Biol. Chem., (Mar. 2010), vol. 285, No. 13, pp. 9429-9436.
Zhu, Huaqing et al., "MicroRNA-195 promotes palmitate-induced apoptosis in cardiomyocytes by down-regulating Sirt1," Cardiovasc. Res., (2011), 92, pp. 75-84.
Chung et al., "Probing structure and function of VLDL by synthetic amphipathic helical peptides," The Journal of Lipid Research, vol. 37, pp. 1099-1112 (May 1996), retrieved from http://www.jlr.org/content/37/5/1099.long.

(56) References Cited

OTHER PUBLICATIONS

Falla et al., "Mode of Action of the Antimicrobial Peptide Indolicidin," The Journal of Biological Chemistry, vol. 271, pp. 19298-19303 (Aug. 9, 1996), retrieved from http://dx.doi.org/10.1074/jbc.271.32.19298.

Ito et al., Transmembrade delivery of polypeptide hormones bypassing the intrinsic cell surface receptors: a conjugate of insulin with a2-macroglobulin (a2M) recognizing both insulin and a2M receptors and its biological activity in relation to endocytic pathways, Molecular and Cellular Endocrinology, 36 (1984) pp. 165-173.

Kang et al., :Stability of the Disulfide Bond in an Avidin-Biotin Linked Chimeric Peptide During in vivo Transcytosis Through Brain Endothelial Cells, Journal of Drug Targeting, vol. 8, pp. 425-436 (Oct. 20, 2008), retrieved from https://doi.org/10.3109/10611860008997918.

Richard, et al., "Cell-penetrating Peptides," Journal of Biological Chemistry, (2003), 278(1), pp. 585-590.

Zhao et al., "Transcellular Transport of a Highly Polar 3 Net Charge Opioid Tetrapeptide," The Journal of Pharmacology and Experimental Terapeutics, vol. 304, No. 1, pp. 435-432, 2003.

\* cited by examiner

SEQUENCE LISTING

```
<160> NUMBER OF SEQ ID NOS: 16

<210> SEQ ID NO 1
<211> LENGTH: 8
<212> TYPE: PRT
<213> ORGANISM: artificial sequence
<220> FEATURE:
<223> OTHER INFORMATION: synthetic peptide

<400> SEQUENCE: 1

Tyr Arg Phe Lys Glu His Trp Arg
1               5

<210> SEQ ID NO 2
<211> LENGTH: 6
<212> TYPE: PRT
<213> ORGANISM: artificial sequence
<220> FEATURE:
<223> OTHER INFORMATION: synthetic peptide

<400> SEQUENCE: 2

Lys Gln Tyr Arg Phe Trp
1               5

<210> SEQ ID NO 3
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: amidation

<400> SEQUENCE: 3

Tyr Arg Phe Lys Glu
1               5

<210> SEQ ID NO 4
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: D-amino acid

<400> SEQUENCE: 4
```

```
Met Tyr Lys Phe Arg
1               5

<210> SEQ ID NO 5
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid

<400> SEQUENCE: 5

His Glu Lys Tyr Phe Arg
1               5

<210> SEQ ID NO 6
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (6)..(6)
<223> OTHER INFORMATION: amidation

<400> SEQUENCE: 6

Lys Gln Tyr Arg Phe Trp
1               5

<210> SEQ ID NO 7
<211> LENGTH: 7
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid

<400> SEQUENCE: 7

Phe Arg Lys Trp Tyr Arg His
1               5

<210> SEQ ID NO 8
<211> LENGTH: 7
<212> TYPE: PRT
<213> ORGANISM: artificial sequence
<220> FEATURE:
<223> OTHER INFORMATION: synthetic peptide
<220> FEATURE:
```

```
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (7)..(7)
<223> OTHER INFORMATION: amidation

<400> SEQUENCE: 8

Gly Phe Lys Tyr His Arg Tyr
1               5

<210> SEQ ID NO 9
<211> LENGTH: 8
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: amidation

<400> SEQUENCE: 9

Val Lys His Tyr Phe Ser Tyr Arg
1               5

<210> SEQ ID NO 10
<211> LENGTH: 8
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid

<400> SEQUENCE: 10

Trp Lys Phe Asp Arg Tyr His Lys
1               5

<210> SEQ ID NO 11
<211> LENGTH: 8
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid and amidation
```

```
<400> SEQUENCE: 11

Lys Trp Tyr Arg Asn Phe Tyr His
1               5

<210> SEQ ID NO 12
<211> LENGTH: 9
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid

<400> SEQUENCE: 12

Thr Gly Tyr Arg His Phe Trp His Lys
1               5

<210> SEQ ID NO 13
<211> LENGTH: 9
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: amidation

<400> SEQUENCE: 13

Asp Trp Lys Tyr His Phe Arg Gly Lys
1               5

<210> SEQ ID NO 14
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (6)..(8)
<223> OTHER INFORMATION: D-amino acid
<220> FEATURE:
<221> NAME/KEY: MISC_FEATURE
<222> LOCATION: (10)..(10)
<223> OTHER INFORMATION: amidation
```

```
<400> SEQUENCE: 14

His Lys Tyr Phe Glu Asp His Lys Arg Trp
1               5                   10

<210> SEQ ID NO 15
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid

<400> SEQUENCE: 15

Ala Phe Arg Tyr Lys Trp His Tyr Gly Phe
1               5                   10

<210> SEQ ID NO 16
<211> LENGTH: 5
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: 2'6' dimethyltyrosine
<220> FEATURE:
<221> NAME/KEY: MISC_FEATURE
<222> LOCATION: (2)..(2)
<223> OTHER INFORMATION: D-amimo acid
<220> FEATURE:
<221> NAME/KEY: MISC_FEATURE
<222> LOCATION: (5)..(5)
<223> OTHER INFORMATION: amidation

<400> SEQUENCE: 16

Tyr Arg Phe Lys Cys
1               5
```

METHOD AND CARRIER COMPLEXES FOR DELIVERING MOLECULES TO CELLS

CROSS-REFERENCE TO RELATED APPLICATIONS

This application is a continuation of U.S. application Ser. No. 13/422,722, filed Mar. 16, 2012, which is a continuation of U.S. application Ser. No. 12/631,048, filed Dec. 4, 2009, now issued as U.S. Pat. No. 8,148,322, which is a continuation of U.S. application Ser. No. 10/838,135, filed on May 3, 2004, now issued as U.S. Pat. No. 7,704,954, which claims priority to U.S. Provisional Application Ser. No. 60/467,516, filed on May 1, 2003. The specifications of which are hereby incorporated by reference in their entirety.

STATEMENT OF GOVERNMENT SUPPORT

This invention was made with government support from the National Institute on Drug Abuse under Grant No. P01-DA-08924. The U.S. Government has certain rights in this invention.

BACKGROUND OF THE INVENTION

Biological cells are generally highly selective as to the molecules that are allowed to pass through the cell membrane. As such, the delivery of compounds, such as small molecules and biological molecules into a cell is usually limited by the physical properties of the compound. The small molecules and biological molecules may, for example, be pharmaceutically active compounds.

The lack of delivery of such molecules, including macromolecules, such as proteins and nucleic acids, into cells in vivo, has been an obstacle to the therapeutic, prophylactic and/or diagnostic use of a large number of potentially effective compounds.

In addition, many compounds which appear promising in vitro, have been discarded as potential drugs due to the lack of ability to deliver the compound effectively inside a cell, in vivo.

Several reports have addressed the problem of delivering compounds to cells by covalently attaching the compounds to "protein transduction domains" (PTDs). Schwarze et al. (*Trends Pharmacol Sci.* 2000; 21:45-8) and U.S. Pat. No. 6,221,355 to Dowdy disclose several PTDs that can cross the lipid bilayer of cells in a concentration-dependent manner. The PTDs disclosed include PTDs derived from the HIV-I tat protein, from a *Drosophila* homeotic transcription factor encoded by the antennapedia (abbreviated ANTP) gene, and from a herpes simplex virus VP22 transcription factor. The HIV-1 tat PTD is eleven amino acids in length, the ANTP PTD is sixteen amino acids in length, and the VP22 PTD is 34 amino acids in length.

Recent publications, however, indicate that these PTDs enter cells via energy-dependent endocytosis. Therefore, the "PTD-cargo" complexes are contained within the cell's endosomal vesicles and not available to, for example, the cytoplasm of the cell. Accordingly, the "PTD-cargo" complexes must be released from the endosomal vesicles in order to be bioactive (Richard et al., 1 Biol. Chem. 2003; 278:585-590; Drin et al., *J. Biol. Chem.,* 2003; 278:31192-31201). Further, there are recent reports that these PTDs are toxic to cells.

Thus, there is a need for peptides which are capable of crossing the lipid membrane of cells in an energy-independent non-endocytotic manner. In addition, in order to avoid immune responses, commonly known for large peptides, there is a need for smaller, peptidase-resistant, peptides. Finally, it is important that the peptide carriers be nontoxic to cells.

SUMMARY OF THE INVENTION

These needs have been met by the present invention which provides a method for delivering a molecule to a cell. The method comprises contacting the cell with a carrier complex, wherein the carrier complex comprises the molecule and an aromatic cationic 20 peptide, and wherein the aromatic cationic peptide comprises:

(a) at least one net positive charge;
(b) a minimum of three amino acids;
(c) a maximum of ten amino acids;
(d) a relationship between the minimum number of net positive charges ($p_m$) and the total number of amino acid residues (r) wherein $3p_m$ is the largest number that is less than or equal to r+1; and
(e) a relationship between the minimum number of aromatic groups (a) and the total number of net positive charges ($p_t$) wherein 3a is the largest number that is less than or equal to $p_t$+1, except that when a is 1, $p_t$ may also be 1.

In another embodiment, the invention provides a carrier complex comprising a molecule and an aromatic cationic peptide, wherein the aromatic cationic peptide comprises:

(a) at least one net positive charge;
(b) a minimum of three amino acids;
(c) a maximum of ten amino acids;
(d) a relationship between the minimum number of net positive charges ($p_m$) and the total number of amino acid residues (r) wherein $3p_m$ is the largest number that is less than or equal to r+1; and
(e) a relationship between the minimum number of aromatic groups (a) and the total number of net positive charges ($p_t$) wherein 3a is the largest number that is less than or equal to $p_t$+1, except that when a is 1, $p_t$ may also be 1.

In yet another embodiment, the invention provides a method for delivering a molecule to a cell. The method comprises contacting the cell with a molecule and an aromatic cationic peptide, wherein the aromatic cationic peptide comprises:

(a) at least one net positive charge;
(b) a minimum of three amino acids;
(c) a maximum of ten amino acids;
(d) a relationship between the minimum number of net positive charges ($p_m$) and the total number of amino acid residues (r) wherein $3p_m$ is the largest number that is less than or equal to r+1; and
(e) a relationship between the minimum number of aromatic groups (a) and the total number of net positive charges ($p_t$) wherein 3a is the largest number that is less than or equal to $p_t$+1, except that when a is 1, $p_t$ may also be 1.

DETAILED DESCRIPTION OF THE INVENTION

Figure 1:
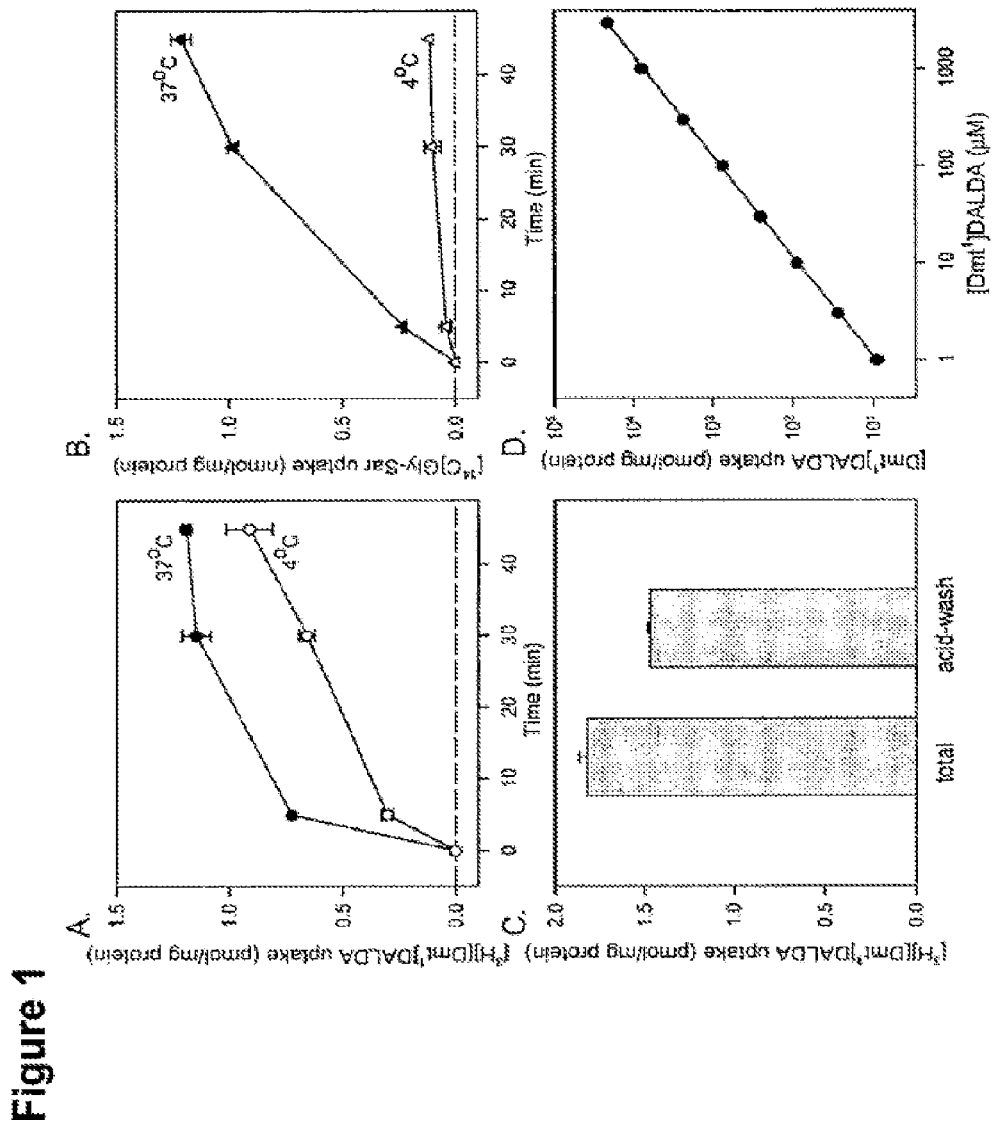
FIG. 1. Peptide uptake in Caco-2 cells. Time course of [$^3$H][Dmt$^1$]DALDA (A) and [$^{14}$C]Gly-Sar (B) uptake. Caco-2 cells were incubated with [$^3$H][Dmt$^1$]DALDA (250 nM, 47 Ci/mmol) or [$^{14}$C]Gly-Sar (50 μM, 56.7 mCi/mmol) for 1 h at either 37 or 4° C. Radioactivity was subsequently determined in solubilized cells. (C) effect of acid-wash on accumulation of [$^3$H][Dmt$^1$]DALDA. Caco-2 cells were incubated with [³H][Dmt¹]DALDA for 1 h at 37° C. Before cell lysis, cells were subjected to acid-wash to remove cell surface-associated radioactivity. (D) effect of [Dmt¹] DALDA concentration on [Dmt¹]DALDA uptake. Cells were incubated with a range of [Dmt¹]DALDA concentrations (1 μM-3 mM) for 1 h at 37° C. All data are presented as mean.±S.E. of three independent monolayers. Where error bars are not apparent, they are smaller than the symbol.

The invention is based on the surprising discovery by the inventors that certain carrier complexes comprising at least one molecule and an aromatic cationic peptide can cross cell membranes by an energy-independent mechanism and deliver the molecules inside the cell.

Aromatic Cationic Peptides

The aromatic cationic peptides useful in the present invention have a net positive charge as described below, are water-soluble and highly polar. The peptides include a minimum of three amino acids, and preferably include a minimum of four amino acids, covalently joined by peptide bonds.

The maximum number of amino acids present in the aromatic cationic peptides is ten, preferably about eight, and most preferably about six. Optimally, the number of amino acids present in the peptides is about four. The term "about" as used in the definition for the maximum number of amino acids means plus or minus one amino acid.

The amino acids of the aromatic cationic peptides useful in the present invention can be any amino acid. As used herein, the term "amino acid" is used to refer to any organic molecule that contains at least one amino group and at least one carboxyl group. Preferably, at least one amino group is at the a position relative to the carboxyl group.

The amino acids may be naturally occurring. Naturally occurring amino acids include, for example, the twenty most common amino acids normally found in proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

Other naturally occurring amino acids include, for example, amino acids that are synthesized in metabolic processes not associated with protein synthesis. For example, the amino acid ornithine is synthesized in mammalian metabolism during the production of urea.

The aromatic cationic peptides useful in the present invention optionally comprise one or more amino acids that are non-naturally occurring. In one embodiment, the peptide has no amino acids that are naturally occurring.

Non-naturally occurring amino acids are those amino acids that typically are not synthesized in normal metabolic processes in living organisms, and do not naturally occur in proteins.

In addition, the non-naturally occurring amino acids useful in the present invention preferably are also not recognized by common proteases. Thus, the non-naturally occurring amino acids are preferably resistant, and more preferably insensitive, to common proteases.

Non-naturally occurring amino acids can be present at any position in the peptide. For example, a non-naturally occurring amino acid can be at the N-terminus, the C-terminus, and/or at any one or more positions between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, .delta.-aminovaleric acid, and .epsilon.-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkoxy (i.e., alkoxy), amino, $C_1$-$C_4$ alkylamino (e.g., methylamino) and $C_1$-$C_4$ dialkylamino (e.g., dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the present invention is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol.

Another such modification includes modification of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids may generally be levorotatory (L-), dextrorotatory (D), or mixtures thereof. Examples of suitable non-naturally occurring amino acids also include the dextrorotatory (D-) form of any of the above-mentioned naturally occurring L-amino acids, as well as L- and/or D-non-naturally occurring amino acids. In this regard, it should be noted that D-amino acids do not normally occur in proteins, although they are found in certain peptide antibiotics that are synthesized by means other than the normal ribosomal protein synthetic machinery of the cell. As used herein, such D-amino acids are considered to be non-naturally occurring amino acids.

In order to minimize protease sensitivity, the peptides useful in the invention should have less than five, preferably less than four, more preferably less than three, and most preferably, less than two contiguous L-amino acids recognized by common proteases, irrespective of whether the amino acids are naturally or non-naturally occurring. In one embodiment, the peptide has only D-amino acids, and no L-amino acids.

If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are cleaved by common proteases, such as endopeptidases and trypsin. Examples of basic amino acids include arginine, lysine and histidine.

It is important that the aromatic cationic peptides have a minimum number of net positive charges at physiological pH in comparison to the total number of amino acid residues in the peptide. The minimum number of net positive charges at physiological pH will be referred to below as $(p_m)$. The total number of amino acid residues in the peptide will be referred to below as $(r)$.

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-Arg (SEQ ID NO: 1) has one negatively charged amino acid (i.e., Glu) and four positively charged amino acids (i.e., two Arg residues, one Lys, and one His). Therefore, the above peptide has a net positive charge of three.

In one embodiment of the present invention, the aromatic cationic peptides have a relationship between the minimum number of net positive charges at physiological pH $(p_m)$ and the total number of amino acid residues (r) wherein $3p_m$ is the largest number that is less than or equal to r+1. In this embodiment, the relationship between the minimum number of net positive charges $(p_m)$ and the total number of amino acid residues (r) is as follows:

| | (r) | | | | | | |
|---|---|---|---|---|---|---|---|
| | 3 | 4 | 5 | 6 | 7 | 8 | 9 | 10 |
| $(p_m)$ | 1 | 1 | 2 | 2 | 2 | 3 | 3 | 3 |

In another embodiment, the aromatic cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

| (r) | | | | | | | |
|---|---|---|---|---|---|---|---|
| 3 | 4 | 5 | 6 | 7 | 8 | 9 | 10 |
| ($p_m$) | | | | | | | |
| 2 | 2 | 3 | 3 | 4 | 4 | 5 | 5 |

In one embodiment, the number of net positive charges ($p_m$) and the number of amino acid residues (r) are equal. In another preferred embodiment, the peptides have three or four amino acid residues and a minimum of one net positive charge, preferably, a minimum of two net positive charges and more preferably a minimum of three net positive charges.

It is also important that the aromatic cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine. For example, the hexapeptide Lys-Gln-Tyr-Arg-Phe-Trp (SEQ ID NO: 2) has a net positive charge of two (contributed by the lysine and arginine residues) and three aromatic groups (contributed by tyrosine, phenylalanine and tryptophan residues).

In one embodiment of the present invention, the aromatic cationic peptides useful in the methods of the present invention have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the number of net positive charges ($p_t$) is as follows:

| ($p_t$) | | | | | | | | | |
|---|---|---|---|---|---|---|---|---|---|
| 1 | 2 | 3 | 4 | 5 | 6 | 7 | 8 | 9 | 10 |
| (a) | | | | | | | | | |
| 1 | 1 | 1 | 1 | 2 | 2 | 2 | 3 | 3 | 3 |

In another embodiment the aromatic cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

| ($p_t$) | | | | | | | | | |
|---|---|---|---|---|---|---|---|---|---|
| 1 | 2 | 3 | 4 | 5 | 6 | 7 | 8 | 9 | 10 |
| (a) | | | | | | | | | |
| 1 | 1 | 2 | 2 | 3 | 3 | 4 | 4 | 5 | 5 |

In another embodiment, the number of aromatic groups (a) and the total number of net positive charges ($p_t$) are equal.

Carboxyl groups, especially the terminal carboxyl group of a C-terminal amino acid, are preferably amidated with, for example, ammonia to form a C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group.

In addition, the free carboxylate groups of amino acid residues having more than one carboxylate group, e.g., asparagine, glutamine, aspartic acid, and glutamic acid residues, may also be amidated wherever they occur. The amidation at these positions may be with ammonia or any of the primary or secondary amines described above.

In one embodiment, the aromatic cationic peptide useful in the methods of the present invention is a tripeptide having two net positive charges and at least one aromatic amino acid. In a particular embodiment, the aromatic cationic peptide useful in the methods of the present invention is a tripeptide having two net positive charges and two aromatic amino acids.

Aromatic cationic peptides useful in the methods of the present invention include, but are not limited to, the following peptide examples:

Lys-D-Arg-Tyr-NH$_2$,

Phe-D-Arg-His,

D-Tyr-Trp-Lys-NH$_2$,

Trp-D-Lys-Tyr-Arg-NH$_2$,

Tyr-His-D-Gly-Met,

Phe-Arg-D-His-Asp, (SEQ ID NO: 3)
Tyr-D-Arg-Phe-Lys-Glu-NH$_2$, (SEQ ID NO: 4)
Met-Tyr-D-Lys-Phe-Arg, (SEQ ID NO: 5)
D-His-Glu-Lys-Tyr-D-Phe-Arg, (SEQ ID NO: 6)
Lys-D-Gln-Tyr-Arg-D-Phe-Trp-NH$_2$, (SEQ ID NO: 7)
Phe-D-Arg-Lys-Trp-Tyr-D-Arg-His, (SEQ ID NO: 8)
Gly-D-Phe-Lys-Tyr-His-D-Arg-Tyr-NH$_2$, (SEQ ID NO: 9)
Val-D-Lys-His-Tyr-D-Phe-Ser-Tyr-Arg-NH$_2$, (SEQ ID NO: 10)
Trp-Lys-Phe-D-Asp-Arg-Tyr-D-His-Lys, (SEQ ID NO: 11)
Lys-Trp-D-Tyr-Arg-Asn-Phe-Tyr-D-His-NH$_2$, (SEQ ID NO: 12)
Thr-Gly-Tyr-Arg-D-His-Phe-Trp-D-His-Lys, (SEQ ID NO: 13)
Asp-D-Trp-Lys-Tyr-D-His-Phe-Arg-D-Gly-Lys-NH$_2$,

-continued

```
                                         (SEQ ID NO: 14)
D-His-Lys-Tyr-D-Phe-Glu-D-Asp-D-His-D-Lys-Arg-

Trp-NH2,
and (SEQ ID NO: 15)
Ala-D-Phe-D-Arg-Tyr-Lys-D-Trp-His-D-Tyr-Gly-Phe.
```

In a particularly preferred embodiment, an aromatic cationic peptide has the formula Tyr-D-Arg-Phe-Lys-NH$_2$ (for convenience represented by the acronym: DALDA). DALDA has a net positive charge of three, contributed by the amino acids tyrosine, arginine, and lysine and has two aromatic groups contributed by the amino acids phenylalanine and tyrosine. The tyrosine of DALDA can be a modified derivative of tyrosine such as in 2',6'-dimethyltyrosine to produce the compound having the formula 2',6'-Dmt-D-Arg-Phe-Lys-NH$_2$ (i.e., Dmt$^1$-DALDA). Other modified derivatives of tyrosine include 2'-methyltyrosine (Mmt); N,2',6'-trimethyltyrosine (Tmt); and 2'-hydroxy-6'-methyltryosine (Hmt).

In another preferred embodiment, the amino acid at the N-terminus of DALDA can be a phenylalanine or its derivative. An aromatic cationic peptide with phenylalanine at the N-terminus has the formula Phe-D-Arg-Phe-Lys-NH$_2$ (i.e., Phe$^1$-DALDA). Preferred derivatives of phenylalanine include 2'-methylphenylalanine (Mmp), 2',6'-dimethylphenylalanine (Dmp), N,2',6'-trimethylphenylalanine (Tmp), and 2'-hydroxy-6'-methylphenylalanine (Hmp).

In another embodiment, the amino acid sequence of Dmt$^1$-DALDA is rearranged such that Dmt is not at the N-terminus. An example of such an aromatic cationic peptide has the formula D-Arg-2'6'Dmt-Lys-Phe-NH$_2$.

Any of the specific peptides mentioned herein, such as those mentioned above and those mentioned below, e.g., in table 1, including Dmt$^1$-DALDA, DALDA, Phe$^1$-DALDA, D-Arg-2',6'Dmt-Lys-Phe-NH$_2$ and their derivatives can further include functional analogs. A peptide is considered a functional analog of Dmt$^1$-DALDA, DALDA, Phe$^1$-DALDA, or D-Arg-2'6'Dmt-Lys-Phe-NH$_2$ if the analog has the same function as Dmt$^1$-DALDA, DALDA, Phe$^1$-DALDA, or D-Arg-2'6'Dmt-Lys-Phe-NH$_2$. The analog may, for example, be a substitution variant of Dmt$^1$-DALDA, DALDA, Phe$^1$-DALDA, or D-Arg-2'6'Dmt-Lys-Phe-NH$_2$, wherein one or more amino acids is substituted by another amino acid.

Suitable substitution variants of Dmt$^1$-DALDA, DALDA, Phe$^1$-DALDA, or D-Arg-2'6'Dmt-Lys-Phe-NH$_2$ include conservative amino acid substitutions. Amino acids may be grouped according to their physicochemical characteristics as follows:

(a) Non-polar amino acids: Ala(A) Ser(S) Thr(T) Pro(P) Gly(G);
(b) Acidic amino acids: Asn(N) Asp(D) Glu(E) Gln(O);
(c) Basic amino acids: His(H) Arg(R) Lys(K);
(d) Hydrophobic amino acids: Met(M) Leu(L) Ile(I) Val(V); and
(e) Aromatic amino acids: Phe(F) Tyr(Y) Trp(W) His (H).

Substitutions of an amino acid in a peptide by another amino acid in the same group is referred to as a conservative substitution. Conservative substitutions tend to preserve the physicochemical characteristics of the original peptide. In contrast, substitutions of an amino acid in a peptide by another amino acid in a different group is generally more likely to alter the characteristics of the original peptide.

Examples of analogs useful in the practice of the present invention include, but are not limited to the aromatic cationic peptides shown in Tables 1 and 2.

TABLE 1

| Amino Acid Position 1 | Amino Acid Position 2 | Amino Acid Position 3 | Amino Acid Position 4 | Amino Acid Position 5 | C-Terminal Modification |
|---|---|---|---|---|---|
| Tyr | D-Arg | Phe | Lys | | NH$_2$ |
| Tyr | D-Arg | Phe | Orn | | NH$_2$ |
| Tyr | D-Arg | Phe | Dab | | NH$_2$ |
| Tyr | D-Arg | Phe | Dap | | NH$_2$ |
| 2'6'Dmt | D-Arg | Phe | Lys | | NH$_2$ |
| 2'6'Dmt | D-Arg | Phe | Lys | Cys | NH$_2$ (SEQ ID NO: 16) |
| 2'6'Dmt | D-Arg | Phe | Lys-NH(CH2)2-NH-dns | | NH$_2$ |
| 2'6'Dmt | D-Arg | Phe | Lys-NH(CH2)2-NH-atn | | NH$_2$ |
| 2'6'Dmt | D-Arg | Phe | dnsLys | | NH$_2$ |
| 2'6'Dmt | D-Cit | Phe | Lys | | NH$_2$ |
| 2'6'Dmt | D-Cit | Phe | Ahp | | NH$_2$ |
| 2'6'Dmt | D-Arg | Phe | Orn | | NH$_2$ |
| 2'6'Dmt | D-Arg | Phe | Dab | | NH$_2$ |
| 2'6'Dmt | D-Arg | Phe | Dap | | NH$_2$ |
| 2'6'Dmt | D-Arg | Phe | Ahp(2-aminoheptanoic | | NH$_2$ |
| Bio-2'6'Dmt | D-Arg | Phe | Lys | | NH$_2$ |
| 3'5'Dmt | D-Arg | Phe | Lys | | NH$_2$ |
| 3'5'Dmt | D-Arg | Phe | Orn | | NH$_2$ |
| 3'5'Dmt | D-Arg | Phe | Dab | | NH$_2$ |
| 3'5'Dmt | D-Arg | Phe | Dap | | NH$_2$ |
| Tyr | D-Arg | Tyr | Lys | | NH$_2$ |
| Tyr | D-Arg | Tyr | Orn | | NH$_2$ |
| Tyr | D-Arg | Tyr | Dab | | NH$_2$ |
| Tyr | D-Arg | Tyr | Dap | | NH$_2$ |
| 2'6'Dmt | D-Arg | Tyr | Lys | | NH$_2$ |
| 2'6'Dmt | D-Arg | Tyr | Orn | | NH$_2$ |
| 2'6'Dmt | D-Arg | Tyr | Dab | | NH$_2$ |
| 2'6'Dmt | D-Arg | Tyr | Dap | | NH$_2$ |
| 2'6'Dmt | D-Arg | 2'6'Dmt | Lys | | NH$_2$ |
| 2'6'Dmt | D-Arg | 2'6'Dmt | Orn | | NH$_2$ |
| 2'6'Dmt | D-Arg | 2'6'Dmt | Dab | | NH$_2$ |
| 2'6'Dmt | D-Arg | 2'6'Dmt | Pap | | NH$_2$ |

TABLE 1-continued

| Amino Acid Position 1 | Amino Acid Position 2 | Amino Acid Position 3 | Amino Acid Position 4 | Amino Acid Position 5 | C-Terminal Modification |
|---|---|---|---|---|---|
| 3'5'Dmt | D-Arg | 3'5'Dmt | Arg | | NH$_2$ |
| 3'5'Dmt | D-Arg | 3'5'Dmt | Lys | | NH$_2$ |
| 3'5'Dmt | D-Arg | 3'5'Dmt | Orn | | NH$_2$ |
| 3'5'Dmt | D-Arg | 3'5'Dmt | Dab | | NH$_2$ |
| Tyr | D-Lys | Phe | Dap | | NH$_2$ |
| Tyr | D-Lys | Phe | Arg | | NH$_2$ |
| Tyr | D-Lys | Phe | Lys | | NH$_2$ |
| Tyr | D-Lys | Phe | Orn | | NH$_2$ |
| 2'6'Dmt | D-Lys | Phe | Dab | | NH$_2$ |
| 2'6'Dmt | D-Lys | Phe | Dap | | NH$_2$ |
| 2'6'Dmt | D-Lys | 'Phe | Arg | | NH$_2$ |
| 2'6'Dmt | D-Lys | Phe | Lys | | NH$_2$ |
| 3'5'Dmt | D-Lys | Phe | Orn | | NH$_2$ |
| 3'5'Dmt | D-Lys | Phe | Dab | | NH$_2$ |
| 3'5'Dmt | D-Lys | Phe | Dap | | NH$_2$ |
| 3'5'Dmt | D-Lys | Phe | Arg | | NH$_2$ |
| Tyr | D-Lys | Tyr | Lys | | NH$_2$ |
| Tyr | D-Lys | Tyr | Orn | | NH$_2$ |
| Tyr | D-Lys | Tyr | Dab | | NH$_2$ |
| Tyr | D-Lys | Tyr | Dap | | NH$_2$ |
| 2'6'Dmt | D-Lys | Tyr | Lys | | NH$_2$ |
| 2'6'Dmt | D-Lys | Tyr | Orn | | NH$_2$ |
| 2'6'Dmt | D-Lys | Tyr | Dab | | NH$_2$ |
| 2'6'Dmt | D-Lys | Tyr | Dap | | NH$_2$ |
| 2'6'Dmt | D-Lys | 2'6'Dmt | Lys | | NH$_2$ |
| 2'6'Dmt | D-Lys | 2'6'Dmt | Orn | | NH$_2$ |
| 2'6'Dmt | D-Lys | 2'6'Dmt | Dab | | NH$_2$ |
| 2'6'Dmt | D-Lys | 2'6'Dmt | Dap | | NH$_2$ |
| 2'6'Dmt | D-Arg | Phe | dnsDap | | NH$_2$ |
| 2'6'Dmt | D-Arg | Phe | atnDap | | NH$_2$ |
| 3'5'Dmt | D-Lys | 3'5'Dmt | Lys | | NH$_2$ |
| 3'5'Dmt | D-Lys | 3'5'Dmt | Orn | | NH$_2$ |
| 3'5'Dmt | D-Lys | 3'5'Dmt | Dab | | NH$_2$ |
| 3'5'Dmt | D-Lys | 3'5'Dmt | Dap | | NH$_2$ |
| Tyr | D-Lys | Phe | Arg | | NH$_2$ |
| Tyr | D-Orn | Phe | Arg | | NH$_2$ |
| Tyr | D-Dap | Phe | Arg | Tyr | NH$_2$ |
| 2'6'Dmt | D-Arg | Phe | Arg | 2'6'Dmt | NH$_2$ |
| 2'6'Dmt | D-Lys | Phe | Arg | 2'6'Dmt | NH$_2$ |
| 2'6'Dmt | D-Orn | Phe | Arg | 2'6'Dmt | NH$_2$ |
| 2'6'Dmt | D-Dab | Phe | Arg | 2'6'Dmt | NH$_2$ |
| 3'5'Dmt | D-Dap | Phe | Arg | 3'5'Dmt | NH$_2$ |
| 3'5'Dmt | D-Arg | Phe | Arg | 3'5'Dmt | NH$_2$ |
| 3'5'Dmt | D-Lys | Phe | Arg | 3'5'Dmt | NH$_2$ |
| 3'5'Dmt | D-Orn | Phe | Arg | 3'5'Dmt | NH$_2$ |
| Tyr | D-Lys | Tyr | Arg | Tyr | NH$_2$ |
| Tyr | D-Orn | Tyr | Arg | Tyr | NH$_2$ |
| Tyr | D-Dab | Tyr | Arg | Tyr | NH$_2$ |
| Tyr | D-Dap | Tyr | Arg | Tyr | NH$_2$ |
| 2'6'Dmt | D-Arg | 2'6'Dmt | Arg | 2'6'Dmt | NH$_2$ |
| 2'6'Dmt | D-Lys | 2'6'Dmt | Arg | 2'6'Dmt | NH$_2$ |
| 2'6'Dmt | D-Orn | 2'6'Dmt | Arg | 2'6'Dmt | NH$_2$ |
| 2'6'Dmt | D-Dab | 2'6'Dmt | Arg | 2'6'Dmt | NH$_2$ |
| 3'5'Dmt | D-Dap | 3'5'Dmt | Arg | 3'5'Dmt | NH$_2$ |
| 3'5'Dmt | D-Arg | 3'5'Dmt | Arg | 3'5'Dmt | NH$_2$ |
| 3'5'Dmt | D-Lys | 3'5'Dmt | Arg | 3'5'Dmt | NH$_2$ |
| 3'5'Dmt | D-Orn | 3'5'Dmt | Arg | 3'5'Dmt | NH$_2$ |
| Mmt | D-Arg | Phe | Lys | Mmt | NH$_2$ |
| Mmt | D-Arg | Phe | Orn | Mmt | NH$_2$ |
| Mmt | D-Arg | Phe | Dab | Mmt | NH$_2$ |
| Mmt | D-Arg | Phe | Dap | Mmt | NH$_2$ |
| Tmt | D-Arg | Phe | Lys | Tmt | NH$_2$ |
| Tmt | D-Arg | Phe | Orn | Tmt | NH$_2$ |
| Tmt | D-Arg | Phe | Dab | Tmt | NH$_2$ |
| Tmt | D-Arg | Phe | Dap | Tmt | NH$_2$ |
| Hmt | D-Arg | Phe | Lys | Hmt | NH$_2$ |
| Hmt | D-Arg | Phe | Orn | Hmt | NH$_2$ |
| Hmt | D-Arg | Phe | Dab | Hmt | NH$_2$ |
| Hmt | D-Arg | Phe | Dap | Hmt | NH$_2$ |
| Mmt | D-Lys | Phe | Lys | Mmt | NH$_2$ |
| Mmt | D-Lys | Phe | Orn | Mmt | NH$_2$ |
| Mmt | D-Lys | Phe | Dab | Mmt | NH$_2$ |
| Mmt | D-Lys | Phe | Dap | Mmt | NH$_2$ |
| Mmt | D-Lys | Phe | Arg | Mmt | NH$_2$ |
| Tmt | D-Lys | Phe | Lys | Tmt | NH$_2$ |
| Tmt | D-Lys | Phe | Orn | Tmt | NH$_2$ |

TABLE 1-continued

| Amino Acid Position 1 | Amino Acid Position 2 | Amino Acid Position 3 | Amino Acid Position 4 | Amino Acid Position 5 | C-Terminal Modification |
|---|---|---|---|---|---|
| Tmt | D-Lys | Phe | Dab | Tmt | NH$_2$ |
| Tmt | D-Lys | Phe | Dap | Tmt | NH$_2$ |
| Tmt | D-Lys | Phe | Arg | Tmt | NH$_2$ |
| Hmt | D-Lys | Phe | Lys | Hmt | NH$_2$ |
| Hmt | D-Lys | Phe | Orn | Hmt | NH$_2$ |
| Hmt | D-Lys | Phe | Dab | Hmt | NH$_2$ |
| Hmt | D-Lys | Phe | Dap | Hmt | NH$_2$ |
| Hmt | D-Lys | Phe | Arg | Hmt | NH$_2$ |
| Mmt | D-Lys | Phe | Arg | Mmt | NH$_2$ |
| Mmt | D-Orn | Phe | Arg | | NH$_2$ |
| Mmt | D-Dab | Phe | Arg | | NH$_2$ |
| Mmt | D-Dap | Phe | Arg | | NH$_2$ |
| Mmt | D-Arg | Phe | Arg | | NH$_2$ |
| Tmt | D-Lys | Phe | Arg | | NH$_2$ |
| Tmt | D-Orn | Phe | Arg | | NH$_2$ |
| Tmt | D-Dab | Phe | Arg | | NH$_2$ |
| Tmt | D-Dap | Phe | Arg | | NH$_2$ |
| Tmt | D-Arg | Phe | Arg | | NH$_2$ |
| Hmt | D-Lys | Phe | Arg | | NH$_2$ |
| Hmt | D-Orn | Phe | Arg | | NH$_2$ |
| Hmt | D-Dab | Phe | Arg | | NH$_2$ |
| Hmt | D-Dap | Phe | Arg | | NH$_2$ |
| Hmt | D-Arg | Phe | Arg | | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = T-hydroxy,6-methyltyrosine
dnsDap = (3-dansyl-L-a,p-diaminopropionic acid
atnDap = P-anthraniloyl-L-a,o-diaminopropionic acid
Bio = biotin

TABLE 2

| Amino Acid Position 1 | Amino Acid Position 2 | Amigo Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Dmt | Lys | NH$_2$ |
| Phe | D-Arg | Lys | Dmt | NH$_2$ |
| Phe | D-Arg | Phe | Lys | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexyl

The amino acids of the peptides shown in Tables 1 and 2 may be in either the L- or the D-configuration.

Further cationic peptides can be found in U.S. Provisional Application No. 60/444,777 filed Feb. 4, 2003, which is hereby incorporated by reference.

Molecules

The molecule can be a biological molecule or a small molecule. Preferably, the biological molecule or small molecule is a pharmaceutically active molecule. A pharmaceutically active molecule as used herein, is any molecule which exerts a beneficial effect in vivo.

A biological molecule is any molecule which contains a nucleic acid or amino acid sequence and has a molecular weight greater than 450. Such nucleic acid and amino acid sequences are referred to herein as "polynucleotides" and "polyamino acids," respectively.

Biological molecules include polynucleotides, peptide nucleic acids, and polyamino acids, such as peptides, polypeptides, and proteins. Examples of biological molecules which are pharmaceutically active include endogenous peptides (e.g., vasopressin, glutathione), proteins (e.g., interferons), hormones (e.g., human growth hormone), enzymes (e.g., α-galactosidase), antibodies (e.g., antibody against beta-amyloid, which can be used to treat Alzheimers disease), neurotrophic growth factors (e.g., nerve growth factor NGF, brain-derived neutrophic factor BDNF), cytokines (e.g., platelet-derived growth factor PDGF, vascular endothelial cell growth factor VEGF), and oligonucleotides.

The oligonucleotides may comprise any sequence of nucleotides, such as DNA or RNA. The DNA and RNA sequences can be single or double-stranded. For example, DNA encoding a protein that is beneficial in assisting survival of a cell during stress can be conjugated to the peptides of the invention. Examples of such proteins include the heat shock proteins (e.g., hsp60, hsp70, etc.).

Examples of single-stranded RNA molecules include ribozymes, RNA decoys, external guide sequences for ribozymes, antisense RNAs and mRNAs. For a review of these single-stranded RNA molecules, see Sullenger et al. (*Nature* 2002, 418: 252-247). The description of these single-stranded RNA molecules, and the description of illnesses and diseases which can be treated with ribozymes, RNA decoys, external guide sequences for ribozymes, antisense RNAs and mRNAs molecules disclosed in Sullenger are hereby incorporated by reference.

An example of double stranded RNA is an RNA interfering molecule (i.e., RNAi such as, for example, siRNA (i.e., small interfering RNA)). The siRNA can be any known to those in the art.

The siRNA can be, for instance, sufficiently complementary to a mRNA to inhibit translation of a protein implicated in a disease, condition or illness. Examples of such proteins include, for instance, β-amyloid which is implicated in Alzheimer's disease and the protein ras which is implicated in cancer.

Alternatively, the siRNA can be, for example, sufficiently complementary to an RNA produced by a virus. The RNA produced by the virus can be any RNA which is generally required for infection of a host cell, survival of the virus, and/or propagation of the virus. Examples of such RNA include Internal Ribosome Entry Site, RNA-dependent polymerase initiation sites, and RNA encoding viral envelope proteins, viral nucleases, and viral proteases.

Examples of viruses include, for example, hepatitis virus, such as hepatitis A, B, and C, human immunodeficiency virus, Epstein-bar virus, cytomegalovirus, and human papilloma virus.

siRNA which target virus RNAs are known to those in the art. For example, siRNAs which target hepatitis C virus RNAs are known to those in the art, see Randall et al. PNAS, 2003, 100: 235-240.

The molecule can be a small molecule. Small molecules include organic compounds, organometallic compounds, salts of organic and organometallic compounds, monosaccharides, amino acids, and nucleotides. Small molecules can further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they do not qualify as biological molecules, and typically have molecular weights less than 450. Small molecules include compounds that are found in nature as well as synthetic compounds. Examples of small molecules which are pharmaceutically active include antibiotics (e.g., tetracycline, penicillin, erythromycin), cytotoxic agents (e.g., doxorubicin, adriamycin), and antioxidants (e.g., vitamin E, vitamin C, beta carotene).

Carrier Complexes

At least one molecule as described above, and at least one aromatic cationic peptide as described above, associate to form a carrier complex. The molecule and aromatic cationic peptide can associate by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

The type of association between the molecules and aromatic cationic peptides typically depends on, for example, functional groups available on the molecule and functional groups available on the aromatic cationic peptide.

For a chemical bond or physical bond, a functional group on the molecule typically associates with a functional group on the aromatic cationic peptide. Alternatively, a functional group on the aromatic cationic peptide associates with a functional group on the molecule.

The functional groups on the molecule and aromatic cationic peptide can associate directly. For example, a functional group (e.g., a sulfhydryl group) on a molecule can associate with a functional group (e.g., sulfhydryl group) on an aromatic cationic peptide to form a disulfide.

Alternatively, the functional groups can associate through a cross-linking agent (i.e., linker). Some examples of cross-linking agents are described below. The cross-linker can be attached to either the molecule or the aromatic cationic peptide.

The linker may and may not affect the number of net charges of the aromatic cationic peptide. Typically, the linker will not contribute to the net charge of the aromatic cationic peptide. Each amino group, if any, present in the linker will contribute to the net positive charge of the aromatic cationic peptide. Each carboxyl group, if any, present in the linker will contribute to the net negative charge of the aromatic cationic peptide.

The number of molecules or aromatic cationic peptides in the carrier complex is limited by the capacity of the peptide to accommodate multiple molecules or the capacity of the molecule to accommodate multiple peptides. For example, steric hindrance may hinder the capacity of the peptide to accommodate especially large molecules. Alternatively, steric hinderance may hinder the capacity of the molecule to accommodate a relatively large (e.g., seven, eight, nine or ten amino acids in length) aromatic cationic peptide.

The number of molecules or aromatic cationic peptides in the carrier complex is also limited by the number of functional groups present on the other. For example, the maximum number of molecules associated with a peptide depends on the number of functional groups present on the peptide. Alternatively, the maximum number of peptides associated with a molecule depends on the number of functional groups present on the molecule.

In one embodiment, the carrier complex comprises at least one molecule, and preferably at least two molecules, associated with an aromatic-cationic peptide. A relatively large peptide (e.g., eight, ten amino acids in length) containing several (e.g., 3, 4, 5 or more) functional groups can be associated with several (e.g., 3, 4, 5 or more) molecules.

In another embodiment, the carrier complex comprises at least one aromatic-cationic peptide, and preferably at least two aromatic cationic peptides, associated with a molecule. For example, a molecule containing several functional groups (e.g., 3, 4, 5 or more) can be associated with several (e.g., 3, 4, or 5 or more) peptides.

In yet another embodiment, the carrier complex comprises one aromatic-cationic peptide associated to one molecule.

In one embodiment, a carrier complex comprises at least one molecule chemically bonded (e.g., conjugated) to at least one aromatic cationic peptide. The molecule can be chemically bonded to an aromatic cationic peptide by any method known to those in the art. For example, a functional group on the molecule may be directly attached to a functional group on the aromatic cationic peptide. Some examples of suitable functional groups include, for example, amino, carboxyl, sulfhydryl, maleimide, isocyanate, isothiocyanate and hydroxyl.

The molecule may also be chemically bonded to the aromatic cationic peptide by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agent include the platinum cross-linking agents described in U.S. Pat. Nos. 5,580,990; 5,985,566; and 6,133,038 of Kreatech Biotechnology, B.V., Amsterdam, The Netherlands.

The functional group on the molecule may be different from the functional group on the peptide. For example, if a sulfhydryl group is present on the molecule, such as in β-galactosidase or in 5'- and/or 3'-end thiol modified DNA and RNA oligonucleotides, the molecule can be cross-linked to the peptide, e.g., [Dmt$^1$]DALDA, through the 4-amino group of lysine by using the cross-linking reagent SMCC (i.e., succinimidyl 4-(N-maleimidomethyl)cyclohexane-1-carboxylate) from Pierce Biotechnology (see Example 10 below). In another example, the 4-amino group of lysine of DALDA can be conjugated directly to an α-phosphate group at the 5'-end of an RNA or DNA oligonucleotide by using the crosslinking reagent EDC (i.e., (N-[3-dimethylaminopropyl-N'-ethylcarboiimide]) from Pierce Biotechnology (see Example 13 below).

Alternatively, the functional group on the molecule and peptide can be the same. Homobifunctional cross-linkers are typically used to cross-link identical functional groups. Examples of homobifunctional cross-linkers include EGS (i.e., ethylene glycol bis[succinimidylsuccinate]), DSS (i.e., disuccinimidyl suberate), DMA (i.e., dimethyl adipimidate.2 HCl), DTSSP (i.e., 3,3'-dithiobis[sulfosuccinimidylpropionate]), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

To chemically bond the molecules and the peptides, the molecules, peptides, and cross-linker are typically mixed together. The order of addition of the molecules, peptides, and cross-linker is not important. For example, the peptide can be mixed with the cross-linker, followed by addition of the molecule. Alternatively, the molecule can be mixed with the cross-linker, followed by addition of the peptide. Optimally, the molecules and the peptides are mixed, followed by addition of the cross-linker.

The chemically bonded carrier complexes deliver the molecules to a cell. In some instances, the molecule functions in the cell without being cleaved from the aromatic cationic peptide. For example, if the aromatic cationic peptide does not block the catalytic site of the molecule, then cleavage of the molecule from the aromatic cationic peptide is not necessary (see Example 11 below).

In other instances, it may be beneficial to cleave the molecule from the aromatic cationic peptide. The web-site of Pierce Biotechnology, Inc. described above can also provide assistance to one skilled in the art in choosing suitable cross-linkers which can be cleaved by, for example, enzymes in the cell. Thus the molecule can be separated from the aromatic cationic peptide. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfo-succinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid.HCl).

In another embodiment, a carrier complex comprises at least one molecule physically bonded with at least one aromatic cationic peptide. Any method known to those in the art can be employed to physically bond the molecules with the aromatic cationic peptides.

For example, the aromatic cationic peptides and molecules can be mixed together by any method known to those in the art. The order of mixing is not important. For instance, molecules can be physically mixed with modified or unmodified aromatic cationic peptides by any method known to those in the art. Alternatively, the modified or unmodified aromatic cationic peptides can be physically mixed with the molecules by any method known to those in the art.

For example, the aromatic-cationic peptides and molecules can be placed in a container and agitated, by for example, shaking the container, to mix the aromatic-cationic peptides and molecules.

The aromatic cationic peptides can be modified by any method known to those in the art. For instance, the aromatic cationic peptide may be modified by means of cross-linking agents or functional groups, as described above. The linker may and may not affect the number of net charges of the aromatic cationic peptide. Typically, the linker will not contribute to the net charge of the aromatic cationic peptide. Each amino group, if any, present in the linker contributes to the net positive charge of the aromatic cationic peptide. Each carboxyl group, if any, present in the linker contributes to the net negative charge of the aromatic cationic peptide.

For example, [Dmt$^1$]DALDA can be modified, through the 4-amino group of lysine by using the cross-linking reagent SMCC (i.e., succinimidyl 4-(N-maleimidomethyl)cyclohexane-1-carboxylate) from Pierce Biotechnology (see Example 10 below). To form a carrier complex, the modified aromatic-cationic peptide is usually formed first and then mixed with the molecule.

One advantage of the physically bonded carrier complexes, is that the molecule functions in a cell without the need for removing an aromatic cationic peptide, such as those carrier complexes in which the molecule is chemically bonded to an aromatic cationic peptide. Furthermore, if the aromatic cationic peptide does not block the catalytic site of the molecule, then dissociation of the complex is also not necessary (see Example 12 below).

Synthesis of the Aromatic Cationic Peptides

The peptides useful in the methods of the present invention may be chemically synthesized by any of the methods well known in the art. Suitable methods for synthesizing the protein include, for example, those described by Stuart and Young in "Solid Phase Peptide Synthesis," Second Edition, Pierce Chemical Company (1984), and in "Solid Phase Peptide Synthesis," Methods Enzymol. 289, Academic Press, Inc, New York (1997).

Modes of Administration

In one embodiment, the invention relates to a method for delivering a molecule to a cell. The method comprises contacting a cell with a molecule and an aromatic cationic peptide. The cell can be contacted with the molecule and aromatic cationic peptide by any method known to those in the art. For example, a cell can be incubated with the molecule and aromatic cationic peptide in vitro. In one aspect, the molecule and aromatic cationic peptide can be present in the form of a carrier complex, such as those carrier complexes described above, comprising chemically bonded or physically bonded molecules and aromatic cationic peptides.

In another embodiment, the method for delivering a molecule to a cell comprises contacting the cell with a carrier complex. The molecule is delivered to the cell by contacting the cell with the carrier complex comprising the molecule and an aromatic cationic peptide. The cell can be contacted with the carrier complex by any method known to those in the art.

For example, a cell can be incubated with the carrier complex in vitro. The cell can be any cell. The cell can be of plant, animal, or bacterial origin. An example of a plant cell includes Arabidopsis cells. Examples of bacterial cells include Saccharomyces and Lactobacillus. Animal cells include mammalian cells, such as neuronal cells, renal epithelial cells, kidney cells, vascular endothelial cells, glial cells, intestinal epithelial cells and hepatocytes. An example of a vascular endothelial cell is a blood brain barrier endothelial cell.

Alternatively, the carrier complex can be administered to a mammal in vivo. An effective amount of a carrier complex, preferably in a pharmaceutical composition, may be administered to a mammal in need thereof by any of a number of well-known methods for administering pharmaceutical compounds.

The carrier complex may be administered systemically or locally. In one embodiment, the carrier complex is administered intravenously. For example, the carrier complex may be administered via rapid intravenous bolus injection. Preferably, however, the carrier complex is administered as a constant rate intravenous infusion.

The carrier complexes may be administered to the tissues of a mammal locally, e.g., by injection into tissues which are accessible by a syringe. For example, if the carrier complex contains a cytotoxic agent which is to be delivered to a tumor in a mammal, preferably, the tumor is accessible to local administration. Such tumors include, for example, skin cancer and breast cancer.

The carrier complex may also be administered orally, topically, intranasally, intramuscularly, subcutaneously, or transdermally. In a preferred embodiment, transdermal administration of carrier complex is by iontophoresis, in which the carrier complex is delivered across the skin by an electric current.

Other routes of administration include intracerebroventricularly or intrathecally. Intracerebroventiculatly refers to administration into the ventricular system of the brain. Intrathecally refers to administration into the space under the arachnoid membrane of the brain or spinal cord. Thus intracerebroventricular or intrathecal administration may be preferred for those diseases and conditions which affect the organs or tissues of the central nervous system.

The carrier complex useful in the methods of the invention may be administered to mammals by sustained release, as is known in the art. Sustained release administration is a method of drug delivery to achieve a certain level of the drug over a particular period of time. The level typically is measured by serum concentration.

Any formulation known in the art of pharmacy is suitable for administration of the carrier complex. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the carrier complex may utilize conventional diluents, carriers, or excipients etc., such as are known in the art can be employed to deliver the carrier complex. For example, the formulations may comprise one or more of the following: a stabilizer, a surfactant, preferably a nonionic surfactant, and optionally a salt and/or a buffering agent. The carrier complex may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the carrier complex.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the carrier complex useful in the methods of the present invention may additionally contain one or more conventional additives. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In a preferred embodiment, the mammal is a human.

Utility

Due to the ability of the carrier complexes to cross cell membranes in an energy-independent mechanism, numerous in vivo and in vitro applications are possible.

The carrier complexes can, for example, be used in vitro, as a research tool. For example, the carrier complexes can deliver molecules, such as proteins, into a cell so that the functional role of the molecule can be studied. Such molecules include, for example, cell signaling proteins (e.g., nuclear factor NF-.kappa.B, kinases, such as JAK).

Another in vitro application includes, for example, the delivery of a marker, such as β-galactosidase, into a cell, such as a stem cell, hemopoietic cell, or embryonic cell, to determine progeny (lineage) of a cell.

Other in vitro applications include, for example, the delivery of a detectable antibody into a cell to determine the presence of a particular protein in the cell.

The carrier complexes also have therapeutic uses in vivo. For example, the aromatic cationic peptides can be used for delivering antisense polynucleotides into a cell of a mammal to down-regulate overexpression of a protein. Further, the aromatic cationic peptides can be used for delivering oligonucleotides for RNA interference (RNAi).

RNAi as used herein refers to a cellular mechanism to regulate the expression of genes or the replication of viruses or bacteria. The mechanism includes the introduction of double stranded RNA (e.g., siRNA) to target a gene's product (typically RNA).

The blood-brain barrier is particularly selective. Thus, another in vivo application include delivering molecules across the blood-brain barrier. Such molecule can include, for example, an antibody to β-amyloid in the treatment of patients with Alzheimers disease.

Typical problems associated with chemotherapeutic agents is achieving adequate levels inside a cell. For example, the chemotherapeutic agent may be too large or the agent may not be aromatic enough to cross the cell membrane. Thus, another in vivo application includes delivering chemotherapeutic agents, such as the cytotoxic agents described above, into a cell.

EXAMPLES

Example 1: Materials and Methods

Drugs and Chemicals.

[Dmt$^1$]DALDA and [$^3$H][Dmt$^1$]DALDA (47 Ci/mmol) were synthesized according to methods described previously (Schiller et al., Eur. J. Med. Chem. 2000, 35: 895-901; Zhao et al., J. Pharmacol. Exp. Ther. 2002, 302: 188-196). [$^{14}$C] Gly-Sar (56.7 mCi/mmol) and [$^3$H][D-Ala$^2$,N-Me-Phe$^4$, Gly$^5$-ol]-enkephalin (50 Ci/mmol) were purchased from Amersham Biosciences (Piscataway, N.J.). All other drugs and chemicals were obtained from Sigma-Aldrich (St. Louis, Mo.).

Cell Culture.

All cell lines were obtained from American Type Culture Collection (Manassas, Va.), and cell culture supplies were obtained from Invitrogen (Carlsbad, Calif.). Caco-2 cells were grown in MEM, whereas SH-SY5Y, HEK293 and Huh7 cells were grown in Dulbecco's modified Eagle's medium. Growing media were supplemented with 10% fetal bovine serum, 200 μg/ml penicillin, and 100 μg/ml streptomycin sulfate. CRFK cells were grown in MEM+10% horse serum, nonessential amino acids, and penicillin/streptomycin. All cell lines were maintained at 37° C. in a humidified atmosphere of 95% air and 5% $CO_2$.

Assay for Peptide Uptake.

Peptide internalization was studied primarily using Caco-2 cells and subsequently confirmed with SH-SY5Y, HEK293, and CRFK cells. Monolayers of cells were grown on 12-well plates ($5 \times 10^5$ cells/well) coated with collagen for 3 days. On day 4, cells were washed twice with prewarmed HBSS, and then incubated with 0.2 ml of HBSS containing either 250 nM [$^3$H][Dmt$^1$]DALDA or 50 μM [$^{14}$C]Gly-Sar at 37° C. for various times up to 1 h. In a separate experiment, cells were incubated with the same concentration of [$^3$H][Dmt$^1$]DALDA in the presence of unlabeled [Dmt$^1$]DALDA (1 μM-3 mM) for 1 h at 37° C. For uptake studies at 4° C., cells were put on ice for 20 min before incubation with [$^3$H][Dmt$^1$]DALDA or [$^{14}$C]Gly-Sar. At the end of the incubation period, cells were washed four times with HBSS, and 0.2 ml of 0.1 N NaOH with 1% SDS was added to each well. The cell contents were then transferred to scintillation vials and radioactivity was counted. An aliquot of cell lysate was used for determination of protein content using the method of Bradford (Bio-Rad, Hercules, Calif.). To distinguish between internalized radioactivity from surface-associated radioactivity, an acid-wash step was included. Before cell lysis, cells were incubated with 0.2 ml of 0.2 M acetic acid/0.05 M NaCl for 5 min on ice.

Assay for Peptide Efflux from CaCo-2 Cells.

Monolayers of Caco-2 cells were grown on 12-well plates ($5 \times 10^5$ cells/well) for 3 days. On day 4, cells were preloaded with [$^3$H][Dmt$^1$]DALDA or [$^{14}$C]Gly-Sar for 1 h at 37° C. Cells were then washed four times with 1 ml of ice-cold incubation solution to terminate uptake and then incubated with 0.5 ml of MEM for 1 h at either 37 or 4° C. to measure the efflux of peptide from cells to the incubation medium. The amount of radioactivity was determined in cell lysates and in the incubation medium. To examine the role of P-glycoprotein on peptide uptake and efflux from cells, [Dmt$^1$]DALDA uptake and efflux were also determined in the presence of 100 μM verapamil (P-glycoprotein inhibitor).

Assay for Peptide Translocation Across Caco-2 Monolayers.

Monolayers of Caco-2 cells were prepared as described previously (Inc et al., J. Pharmacol. Exp. Ther. 2001, 298: 711-717). Caco-2 cells ($2 \times 10^5$) were seeded on microporous membrane filters (24 mm, 0.4 μM) inside Transwell cell culture chambers (Corning Glassworks, Corning, N.Y.). Each Transwell chamber was filled with 1.5 ml of medium in the apical compartment and 2.5 ml in the basolateral compartment. The cell monolayers were given fresh medium every 1 to 2 days and were used on day 28 for transport experiments. Apical-to-basolateral transport of peptides was determined by adding 0.2 μM [$^3$H][Dmt$^1$] DALDA or 100 μM [$^{14}$C]Gly-Sar to the apical compartment, and 50-μl aliquots were removed from both apical and basolateral compartments at various times after peptide addition for determination of radioactivity counts.

The apparent permeability coefficient was calculated according to the following equation: $P_{app} = X/(t \cdot A \cdot Co)$, where X/t is the rate of uptake in the receiver compartment, A is the diffusion area (4.72 cm$^2$), and Co is the initial concentration in the donor compartment.

Confocal Laser Scanning Microscopy.

The uptake of aromatic-cationic peptides into cells was confirmed by confocal laser scanning microscopy (CLSM) using two fluorescent peptides, [Dmt$^1$,dnsDap$^4$]DALDA (Dmt-D-Arg-Phe-dnsDap-NH$_2$, where dnsDap is β-dansyl-1-α-β-diamino-propionic acid) and [Dmt$^1$,atnDap$^4$] DALDA (Dmt-D-Arg-Phe-atnDap-NH$_2$, where atn is β-anthraniloyl-L-α-β-diaminopropionic acid). Caco-2 cells or SH-SY5Y cells were grown as described above and were plated on (35-mm) glass bottom dishes (MatTek, Ashland, Mass.) for 2 days. The medium was then removed, and cells were incubated with 1 ml of HBSS containing 0.1 μM of the fluorescent peptide at either 4° C. or 37° C. for 15 min. Cells were then washed three times with ice-cold HBSS and covered with 200 μl of PBS, and microscopy was performed within 10 min at room temperature using a confocal laser scanning microscope with a C-Apochromat 63x/1.2 W corr objective (Nikon, Tokyo, Japan). Excitation/emission wavelengths were set at 340/520 nm for [Dmt$^1$,dnsDap$^4$]DALDA and 320/420 nm for [Dmt$^1$,atnDap$^4$]-DALDA, respectively. For optical sectioning in z-direction, 5 to 10 frames with 2.0 μM were made.

Radioligand Binding Assay Using Cell Membranes.

Specific binding of [$^3$H][Dmt$^1$]DALDA to cell surface receptors was determined using membranes prepared from Caco-2 and SH-SY5Y cells. After 4 days of culture, cells were washed two times with PBS buffer and then scraped off. Cells were centrifuged at 500 g for 5 min and the pellet stored at −80° C. Cells were homogenized in ice-cold 50 mM Tris-HCl buffer (5 μg/ml leupeptin, 2 μg/ml chymostatin, 10 μg/ml bestatin, and 1 mM EGTA, pH 7.4). The homogenate was centrifuged at 36,000 g for 20 min. The pellets were resuspended with 50 mM Tris-HCl buffer. Aliquots of membrane homogenates (~140 μg of protein) were incubated with [$^3$H][Dmt$^1$]DALDA (15-960 pM) for 60 min at 25° C. Nonspecific binding was assessed by inclusion of 1 μM unlabeled [Dmt$^1$]DALDA. Free radioligand was separated from bound radioligand by rapid filtration through GF/B filters (Whatman, Maidstone, UK) with a cell harvester (Brandel Inc., Gaithersburg, Md.). Filters were washed three times with 10 ml of Tris buffer, and radioactivity was determined by liquid scintillation counting. Binding affinities ($K_d$) and receptor number ($B_{max}$) were determined using nonlinear regression (GraphPad Software, San Diego, Calif.).

Conjugation of Protein to [Dmt1]DALDA.

[Dmt$^1$]DALDA was cross-linked to β-galactosidase (recombinant E. coli, Sigma-Aldrich) using a cross-linker SMCC (succinimidyl 4-(N-maleimidomethyl)cyclohexane-1-carboxylate)(Pierce). SMCC reacts with amine-containing molecules (Lys$^4$ of [Dmt$^1$]DALDA) to form stable amide bonds. Its maleimide end can then be conjugated to a sulfhydryl-containing compound to create a thioether linkage (Bioconjugate Techniques by Greg T. Hermanson, Academic Press, page 234-237). β-Gal contains abundant free sulfhydryl groups in its native state. The uptake of β-Gal provides a convenient read-out with the use of X-gal. Briefly, 1 ml of 5×10$^{-3}$M [Dmt$^1$]DALDA was mixed with 1 mg SMCC in phosphate buffer for 1 h at room temperature. This should result in "activated peptide." The "activated peptide" was diluted 1:10 with phosphate buffer. 1 mg of β-Gal was added to 1 ml of the 1:10 "activated peptide" and mixed at 4° C. for either 2 h or overnight.

Coupling of [Dmt1]DALDA to Cross-Linker SMCC and Confirmation by Mass Spectrometry.

SMCC (1 μg) and [Dmt$^1$]DALDA (5 μg) were dissolved together in 2 ml of PBS, incubated at room temperature for 30 min, and stored at 4° C. An aliquot of the sample was mixed with matrix (saturated 3-hydroxy picolinic acid (HPA) in 50% acetonitrile, 10 mg/ml ammonium citrate) in a 1:10 ratio, and spotted on a stainless steel target plate. Samples were analyzed by Matrix Assisted Laser Desorption Ionization-Time-of-Flight Mass Spectrometry (MALDI-TOF MS) (Applied Biosystems (Voyager DE Pro)) in the positive Reflectron mode.

Conjugation of RNA to [Dmt1]DALDA and Confirmation by Gel Electrophoresis.

Synthetic RNA oligo (40 nucleotides long) was phosphorylated at the 5' end using γ-$^{32}$P-ATP and polynucleotide kinase. The product was purified by gel electrophoresis. 500,000 cpm of gel-purified RNA oligo was conjugated with [Dmt$^1$]DALDA in the presence of 1 mg EDC (N-[3-dimethylaminopropyl-N'-ethylcarboiimide]). The product of the conjugation reaction ([Dmt$^1$]DALDA-RNA oligo) and RNA oligo alone were analyzed on 15% polyacrylamide urea gel.

Conjugation of DNA to [Dmt1]DALDA and Confirmation by Mass Spectrometry.

SMCC (1 μg) and [Dmt$^1$]DALDA (5 μg) were dissolved together in 2 ml of PBS, incubated at room temperature for 30 min, and mixed with deprotected 3'-thiol DNA oligo at 4° C. for 24 hours. After incubation, an aliquot of sample was mixed with matrix (saturated 3-hydroxy picolinic acid (HPA) in 50% acetonitrile, 10 mg/ml ammonium citrate) in a 1:10 ratio, and spotted on a stainless steel target plate. Samples were analyzed by MALDI-TOF MS.

Carrier complex formation by physical mixing of RNA and [Dmt$^1$]DALDA-SMCC conjugate. The [Dmt$^1$]DALDA-SMCC conjugate was prepared as described above. The RNA molecules were mixed with the [Dmt$^1$]DALDA-SMCC conjugate in PBS for 15 min at room temperature before use in cellular uptake studies.

Carrier Complex Formation by Physical Mixing of Protein and [Dmt1]DALDA-SMCC Conjugate.

The [Dmt$^1$]DALDA-SMCC conjugate was prepared as described above. The protein molecules (i.e. Green fluorescent protein, GFP) were mixed with the [Dmt$^1$]DALDA-SMCC conjugate for 15 min at room temperature before use in cellular uptake studies.

Assay for [Dmt1]DALDA-RNA Conjugate Uptake into Cells.

Synthetic RNA oligos were phosphorylated at the 5' end using γ-$^{32}$P-ATP and polynucleotide kinase, and the products were purified by gel electrophoresis. 500,000 cpm of gel-purified RNA oligo was conjugated with [Dmt$^1$] DALDA in the presence of 1 mg N-(3-dimethylaminopropyl-N'-ethylcarboiimide, EDC). Caco-2 cells (1×10$^6$) were washed three times in DMEM medium and pre-incubated in DMEM for 5 minutes. Cells were then incubated with [Dmt$^1$]DALDA-[$^{32}$P]RNA oligo conjugate or unconjugated RNA (approximately 20,000 cpm) for 60 minutes at 37° C. After incubation, the cells were washed three times in DMEM, incubated with lysis buffer, and radioactivity determined in the cell lysate.

Assay for Uptake of RNA Uptake into Cells when Mixed with [Dmt1]DALDA-Cross-Linker Conjugate.

Huh7 cells (1×10$^6$ cells/well) were washed with DMEM and then incubated with 1.0 ml DMEM containing [$^{32}$P] RNA oligo alone or with 40 μl [Dmt$^1$]DALDA-SMCC conjugate, for 60 min at 37° C. Or 4° C. Cells were then washed four times in DMEM and one time in sodium acetate solution to reduce nonspecific binding before incubated in lysis buffer for 30 min and radioactivity determined in the cell lysate.

Assay for [Dmt1]DALDA-Protein Conjugate Uptake into Cells.

Cells (N$_2$A neuroblastoma cells or Caco-2) were plated in 96-well plates (2×10$^4$ cells/well) and incubated with [Dmt$^1$] DALDA cross-linked β-Gal or β-Gal alone for 1 h at 37° C. Cells were then washed 4 times with PBS. The cells were then stained with β-gal staining set (Roche) for at least 2 h at 37° C. And examined under the microscope.

Assay for Protein Uptake into Cells when Co-Incubated with [Dmt1]DALDA-SMCC Conjugate.

Huh7 cells (1×10⁴ cells/well) were washed with DMEM and then incubated with 0.5 ml DMEM containing 3 µg green fluorescent protein (GFP) alone (A), 3 µg GFP and 40 µl [Dmt$^1$]DALDA (B), or 3 µg GFP and 40 µl [Dmt$^1$] DALDA conjugated to SMCC(C) for 60 min at 37° C. 2 ml of cell medium was then added to cells which were incubated for an additional 24 hours in the cell culture incubator. After incubation, cells were washed four times in cell medium and GFP retained in living cells was visualized by confocal laser scanning microscopy. Excitation was performed at 340 nm and emission was measured at 520 nm.

Assay for Apoptosis.

Apoptosis was determined with the use of Hoechst dye (Molecular Probes, Eugene, Oreg.) for staining apoptotic nuclei. The Hoechst dye was loaded to cell cultures and incubated for 15 min. Excessive Hoechst dye was removed by washing cells with cell medium (free of pH indicator) the cells examined using fluorescent microscopy (excitation at 350 nm and emission at 461 nm).

Example 2: Time Course of Uptake of [Dmt$^1$]DALDA and Gly-Sar into Caco-2 Cells When incubated with Caco-2 cells at 37° C., [$^3$F][Dmt$^1$] DALDA was observed in cell lysate as early as 5 min, and steady-state levels were achieved by 30 min (FIG. 1A). The total amount of [$^3$H][Dmt$^1$]DALDA recovered in the cell lysate after 1-h incubation represented about 1% of the total drug. In contrast, under the same experimental conditions, [$^{14}$C]Gly-Sar continued to increase from 5 to 45 min (FIG. 1B). The measured radioactivity is believed to reflect [Dmt$^1$] DALDA levels, because we have previously demonstrated that [Dmt$^1$]DALDA is resistant against peptidase degradation (Szeto et al., J. Pharmacol. Exp. Ther., 2001, 298: 57-61). To determine whether the measured radioactivity was associated with cell membranes, cells were subjected to acid-wash to remove surface binding. FIG. 1C shows that 80.8% of [$^3$H][Dmt$^1$]DALDA was resistant to acid-wash and therefore presumed to be inside the cell. The uptake of [Dmt$^1$]DALDA was found to be concentration-dependent over a wide range of concentrations (FIG. 1D).

Figure 2:
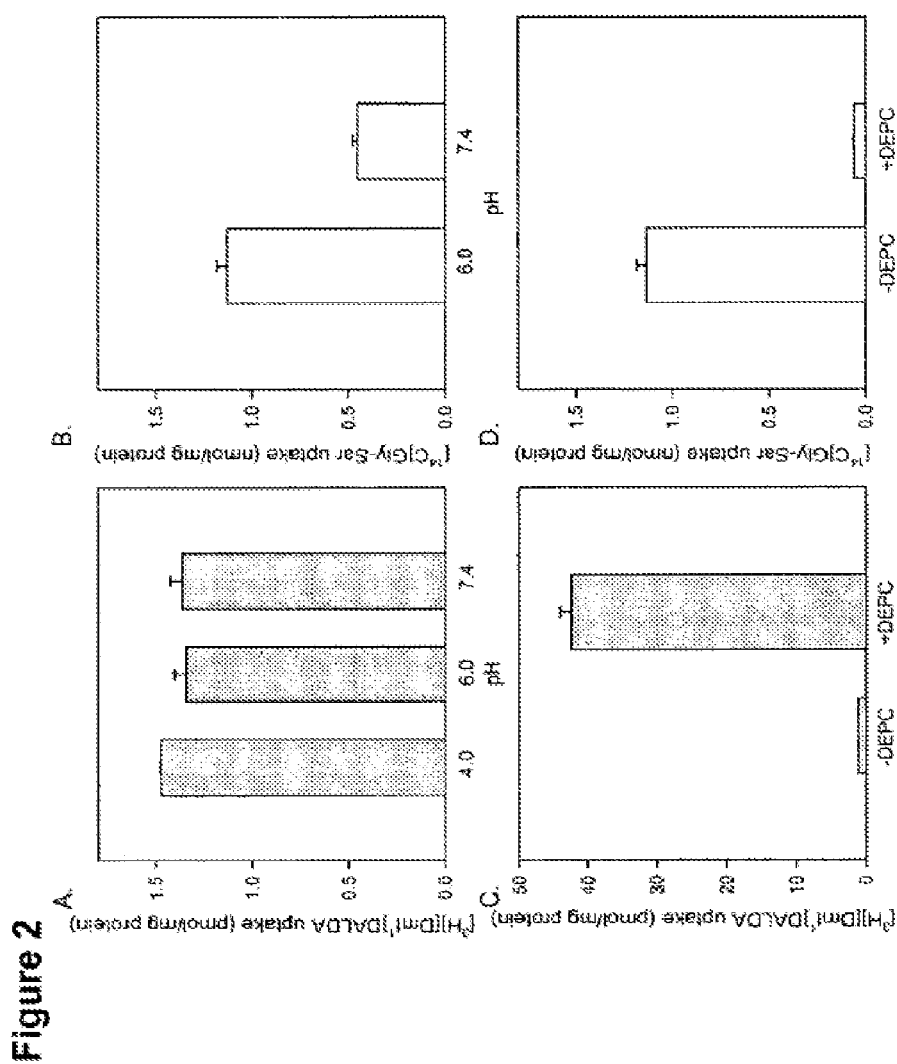
FIG. 2. Effect of pH and DEPC on [³H][Dmt¹]DALDA (A and C) and [¹⁴C]Gly-Sar (B and D) uptake in Caco-2 cells. Caco-2 cells were incubated with [³H][Dmt¹]DALDA (250 nM, 47 Ci/mmol) or [¹⁴C]Gly-Sar (50 μM, 56.7 mCi/mmol) for 1 h at 37° C. under various pH conditions (A and B). Cells were preincubated at 25° C. with 0.2 mM DEPC for 10 min before incubation with [³H][Dmt¹]DALDA (250 nM, 47 Ci/mmol) or [¹⁴C]Gly-Sar (50 μM, 56.7 mCi/mmol) at 37° C. for 1 h (C and D). All data are presented as mean±S.E. of three independent monolayers.

Example 3: Temperature Dependence and Effects of pH on Uptake of [Dmt$^1$]DALDA and Gly-Sar When the incubation was carried out at 4° C., the uptake of [$^3$H][Dmt$^1$]DALDA was slower compared with 37° C., but reached 76.5% by 45 min (FIG. 1A) and 86.3% by 1 h (FIG. 1A). In contrast, the uptake of [$^{14}$C]Gly-Sar was completely abolished at 4° C. (FIG. 1B). The uptake of Gly-Sar by PEPT1 is known to be pH-dependent, with optimal uptake occurring at pH 6.0 (Terada et al., 1999, Am. J. Physiol. 276: G1435-G1441). This was confirmed in our study (FIG. 2B). In contrast, the uptake of [$^3$H][Dmt$^1$] DALDA was unchanged when pH varied from 4.0 to 7.4 (FIG. 2A). The lack of temperature and pH dependence suggests that the uptake of [Dmt$^1$]DALDA in Caco-2 cells is not mediated via PEPT1 (peptide transporter 1).

Example 4: Effect of DEPC on [Dmt$^1$]DALDA and Gly-Sar Uptake

To further demonstrate that PEPT1 is not involved in the transport of [Dmt$^1$]DALDA, we examined the effect of DEPC (diethylpyrocarbonate; 0.2 mM) on [$^3$H][Dmt$^1$] DALDA and [$^{14}$C]Gly-Sar uptake. DEPC is a histidine residue-modifier reagent that has been shown to inhibit PEPT1 in Caco-2 cells (Terada et al., FEBS. Lett., 1996, 394: 196-200). The addition of DEPC to the incubation medium significantly inhibited [$^{14}$C]Gly-Sar uptake (FIG. 2D). Surprisingly, DEPC not only did not inhibit [$^3$H][Dmt$^1$] DALDA uptake but also it actually increased [Dmt$^1$] DALDA uptake by 34-fold (FIG. 2C).

Example 5: [Dmt$^1$]DALDA Internalization in Different Cell Types

Figure 3:
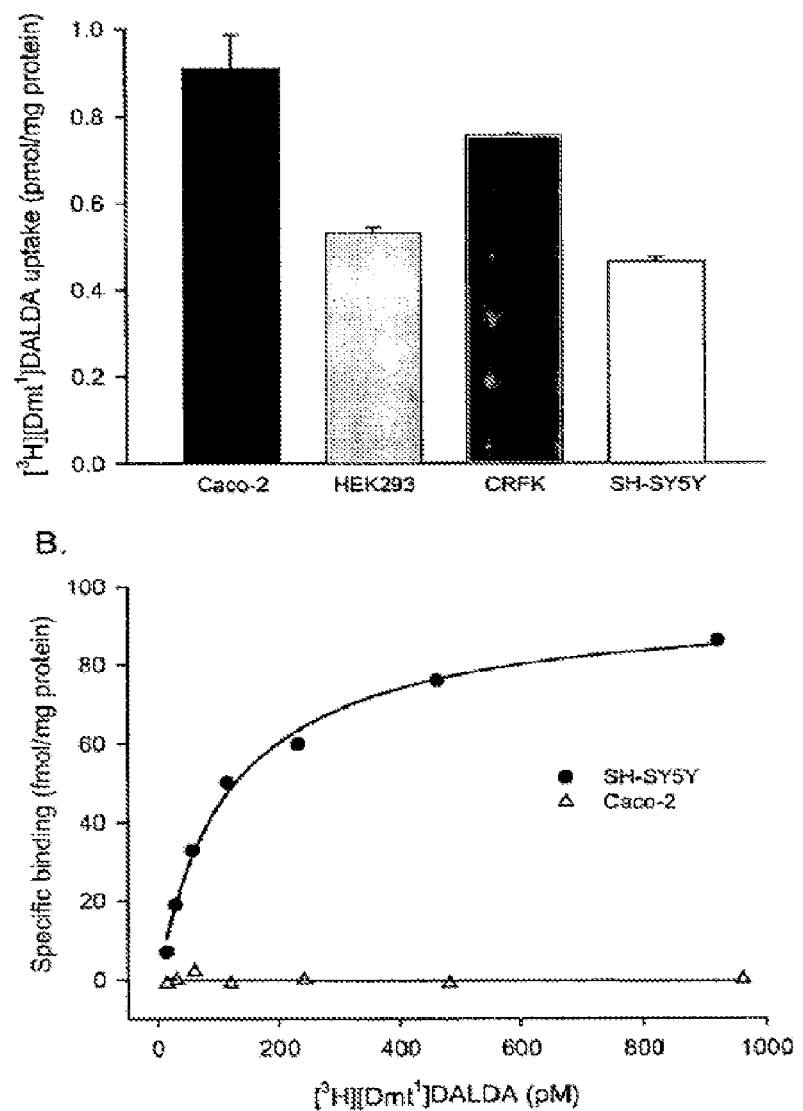
FIG. 3. (A) uptake of [³H][Dmt¹]DALDA in different cell lines. Cells were incubated with [³H][Dmt¹]DALDA (250 nM, 47 Ci/mmol) for 1 h at 37° C. Before cell lysis, cells were subjected to acid-wash to remove cell surface-associated radioactivity. Data shown represent acid-resistant radioactivity and are presented as mean±S.E. for three independent monolayers. (B) specific binding of [³H][Dmt¹] DALDA to cell membranes. Membranes prepared from SH-SY5Y cells and Caco-2 cells were incubated with [³H] [Dmt¹]DALDA (15-960 pM) for 1 h at 25° C. Nonspecific binding was assessed by inclusion of 1 μM unlabeled [Dmt¹]DALDA. Free radioligand was separated from bound radioligand by rapid filtration. No specific binding was observed with Caco-2 cells. For SH-SY5Y cells, the Kd value was 118 pM (range 87-149) and the $B_{max}$ value was 96 fmol/mg protein.

To demonstrate that the internalization of [Dmt$^1$]DALDA was not limited to Caco-2 cells, we compared the internalization of [Dmt$^1$]DALDA in several different cell lines. An acid-wash step was included to distinguish internalized radioactivity (acid-resistant) from surface-bound radioactivity (acid-sensitive). FIG. 3A compares the levels of acid-resistant radioactivity in Caco-2, SH-SY5Y, HEK293, and CRFK cells. The results show that [$^3$H][Dmt$^1$]DALDA was taken up extensively in all cell types.

Example 6: Radioligand Binding Assays with [$^3$H] [Dmt$^1$]DALDA

To determine whether [Dmt$^1$]DALDA was internalized via receptor-mediated mechanisms, we carried out radioligand ([$^3$H][Dmt$^1$]DALDA) binding assays with membranes prepared from Caco-2 cells and SH-SY5Y cells. FIG. 3B shows the specific binding of [$^3$H][Dmt$^1$]DALDA to SH-SY5Y membranes. The calculated $K_d$ value was 118 pM (range 87-149) and the $B_{max}$ value was estimated to be 96 fmol/mg protein (range 88-104). This is comparable with the values obtained using recombinant human µ-opioid receptor expressed on Chinese hamster ovary cells (G.-M. Zhao and H. H. Szeto, unpublished data). No high-affinity specific binding was observed with Caco-2 membranes (FIG. 3B). It is known that HEK293 cells do not have opioid receptors (Blake et al., J. Biol. Chem., 1997, 272: 782-790).

Example 7: Efflux of [Dmt$^1$]DALDA and Gly-Sar from Caco-2 Cells

Figure 4:
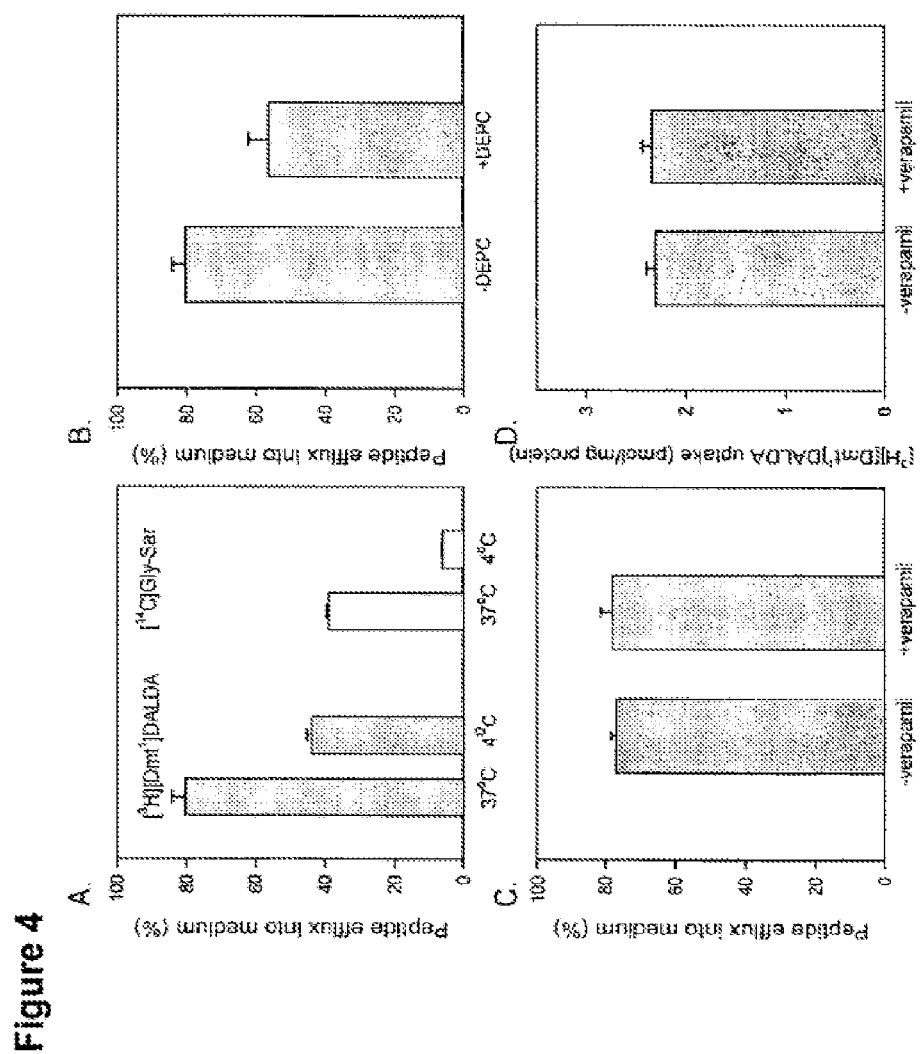
FIG. 4. (A) efflux of [³H][Dmt¹]DALDA (filled column) and [¹⁴C]Gly-Sar (open column). Caco-2 cells were pre-loaded with [³H][Dmt¹]DALDA (250 nM, 47 Ci/mmol) or [¹⁴C]Gly-Sar (50 μM, 56.7 mCi/mmol) for 1 h at either 37 or 4° C. Cells were then washed and incubated with culture medium for 1 h at either 37 or 4° C. Radioactivity was determined in both medium and cell lysate, and the data are presented as percentage of peptide effluxed into medium. (B) effect of DEPC on [³H][Dmt¹]DALDA efflux. Cells were preincubated with 0.2 mM DEPC for 10 min at 25° C. before loading with [³H][Dmt¹]DALDA. (C) effect of verapamil, an inhibitor of p-glycoprotein, on efflux (C) and uptake (D) of [³H][Dmt¹]DALDA-.

The achievement of steady-state [$^3$H][Dmt$^1$]DALDA levels in Caco-2 cells after <30 min of incubation suggested that the rate of efflux of the peptide from the cell was equal to the rate of uptake at that time. To examine the efflux of Gly-Sar and [Dmt$^1$]DALDA from the cell, Caco-2 cells were preloaded with [$^{14}$C]Gly-Sar or [$^3$H][Dmt$^1$]DALDA and then replaced with fresh medium that did not contain peptide. FIG. 4A shows that 39% of [$^{14}$C]Gly-Sar was found in the medium after 1 h at 37° C. The efflux of [$^{14}$C]Gly-Sar was significantly reduced at 4° C. The efflux of [$^3$H][Dmt$^1$] DALDA from Caco-2 cells was much faster, with 80% of the peptide effluxed into the medium by 1 h (FIG. 4A). In contrast to the internalization of [$^3$H][Dmt$^1$]DALDA (FIG. 1A), temperature had a significant effect on the efflux of [$^3$H][Dmt$^1$]DALDA from the cell (FIG. 4A). The efflux of [Dmt$^1$]DALDA was decreased in cells treated with DEPC (FIG. 4B). The reduction in [$^3$H][Dmt$^1$]DALDA efflux by DEPC is consistent with the greatly increased uptake of [$^3$H][Dmt$^1$]DALDA in the presence of DEPC (FIG. 2C). On the other hand, the efflux of [$^3$H][Dmt$^1$]DALDA was not affected by verapamil, an inhibitor of P-glycoprotein (FIG. 4C). Verapamil also had no effect on cellular uptake of [$^3$H][Dmt$^1$]DALDA (FIG. 4D).

The efflux of [Dmt¹]DALDA out of the cell may be beneficial if upon enzymatic cleavage after cellular uptake of the [Dmt¹]DALDA-protein conjugate, [Dmt¹]DALDA is effluxed out of the cell while the protein cargo remains inside.

Example 8: Transcellular Transport of [Dmt¹]DALDA and Gly-Sar

Figure 5:
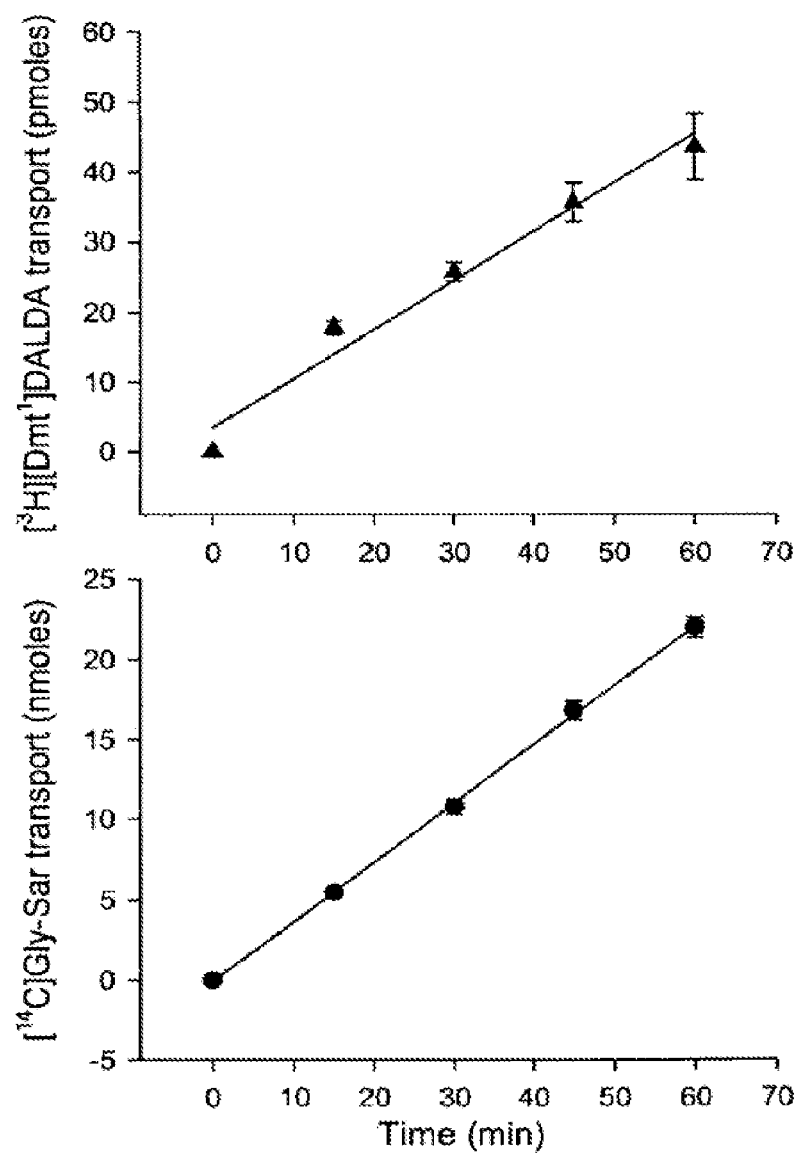
FIG. 5. Transport of [³H][Dmt¹]DALDA and [¹⁴C]Gly-Sar across a Caco-2 monolayer. Caco-2 cells (2×10⁵) were seeded on microporous membrane inside Transwell cell culture chambers. Apical-to-basolateral transport of peptides was determined by adding [³H][Dmt¹]DALDA or [¹⁴C]Gly-Sar to the apical compartment, and 20-μl aliquots were removed from both apical and basolateral compartments at various times after peptide addition for determination of radioactivity.

Caco-2 monolayers grown in Transwells were used to study the apical-to-basolateral transport of [$^3$H][Dmt¹]DALDA and [$^{14}$C]Gly-Sar. FIG. 5 illustrates the transport of [$^{14}$C]Gly-Sar and [$^3$H][Dmt¹]DALDA in the basolateral side at various times after loading the peptide in the apical side of the Transwell. The percentage of [$^3$H][Dmt¹]DALDA translocated from the apical to the basolateral side in 60 min (10.4%) was comparable with the percentage of [$^{14}$C]Gly-Sar transported (11.9%). The apparent permeability coefficient was estimated to be $1.24 \times 10^{-5}$ cm/s for [Dmt¹]DALDA and $1.26 \times 10^{-5}$ cm/s for Gly-Sar.

Figure 6:
FIG. 6. Cellular uptake of [Dmt¹,dnsDap⁴]DALDA and [Dmt¹, atnDap⁴]DALDA. Caco-2 cells were incubated with 0.1 μM [Dmt¹,dnsDap⁴]DALDA for 15 min at 37° C. Cells were then washed and covered with PBS. Microscopy was carried out within 10 min at room temperature. Excitation was performed at 340 nm and emission was measured at 520 nm. The fluorescence appeared diffuse throughout the cytoplasm but was completely excluded from the nucleus. The lack of vesicular concentration at 37° C. suggests non-endocytotic uptake.

Example 9: Visualization of Cellular Uptake of Aromatic-Cationic Peptides Using CLSM To visualize the uptake and mode of cellular internalization of aromatic-cationic peptides, two fluorescent peptides ([Dmt¹,dnsDap⁴]DALDA and [Dmt¹,atnDap⁴]DALDA) were studied by CLSM. FIG. 6 shows the internalization of the fluorescent peptide into Caco-2 cells after incubation with 0.1 µM [Dmt¹,dnsDap⁴]DALDA for 15 min at 37° C. The fluorescence appeared diffuse throughout the cytoplasm with no apparent vesicular distribution, suggesting that the uptake of the peptide did not involve endocytosis and the peptide is not enclosed in an endosome. Note also that the peptide was completely excluded from the nucleus. The internalization of [Dmt¹,atnDap⁴]DALDA into SH-SY5Y cells after incubation with 0.1 µM [Dmt¹,atnDap⁴]DALDA for 30 min at 4° C. clearly support a energy-independent non-endocytotic uptake mechanism, because endocytosis is an energy-dependent process.

Figure 7:
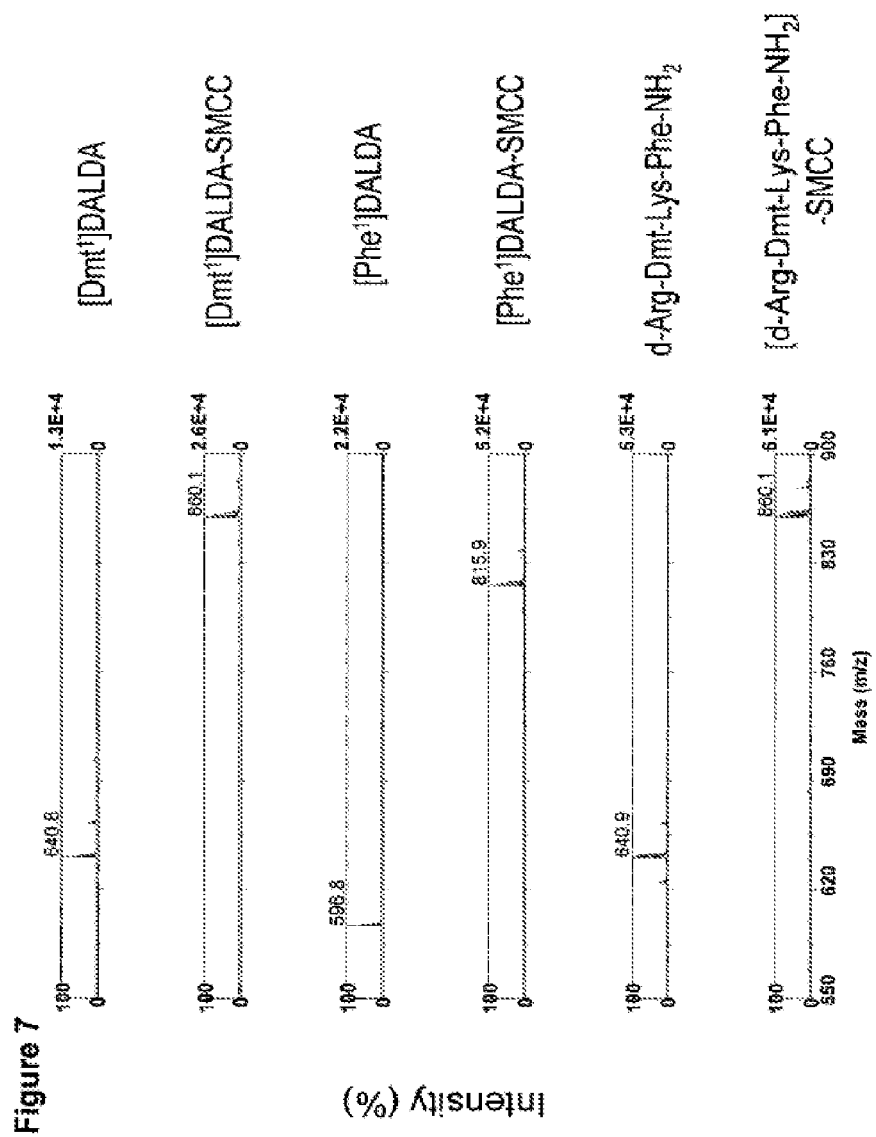
FIG. 7. Mass spectrometric confirmation of coupling of three peptides to cross-linker SMCC. SMCC (1 μg) and peptide (5 μg) were dissolved together in 2 ml of PBS, incubated at room temperature for 30 min, and stored at 4° C. An aliquot of sample was mixed with matrix (saturated 3-hydroxy picolinic acid (HPA) in 50% acetonitrile, 10 mg/ml ammonium citrate) in a 1:10 ratio, and spotted on a stainless steel target plate. Samples were analyzed by Matrix Assisted Laser Desorption Ionization Time-of-Flight Mass Spectrometry (MALDI-TOF MS). The molecular weights of the peptides and their respective SMCC conjugates are indicated on the spectra.

Example 10: Coupling of Peptides to Cross-Linker SMCC and Confirmation by Mass Spectrometry SMCC (1 µg) and 5 µg of [Dmt¹]DALDA, [Phe¹]DALDA, or [d-Arg-Dmt-Lys-Phe-NH$_2$] were dissolved together in 2 ml of PBS, incubated at room temperature for 30 min, and stored at 4° C. An aliquot of the sample was mixed with matrix (saturated 3-hydroxy picolinic acid (HPA) in 50% acetonitrile, 10 mg/ml ammonium citrate) in a 1:10 ratio, and spotted on a stainless steel target plate. Samples were analyzed by Matrix Assisted Laser Desorption Ionization-Time-of-Flight Mass Spectrometry (MALDI-TOF MS) (Applied Biosystems (Voyager DE Pro)) in the positive Reflectron mode. The molecular weights of the peptides and their respective peptide-SMCC conjugates are indicated on the mass spectra (FIG. 7).

Example 11: Peptide Conjugated to a Protein Carlo Brings the Protein Cargo into Cells Various peptides were cross-linked to β-galactosidase (recombinant E. coli, Sigma-Aldrich) using a cross-linker SMCC (Pierce). SMCC reacts with amine-containing molecules (Lys⁴ of [Dmt¹]DALDA) to form stable amide bonds. The formation of peptide-SMCC conjugates is confirmed by mass spectrometry (FIG. 7). Its maleimide end can then be conjugated to a sulfhydryl-containing compound to create a thioether linkage (Bioconjugate Techniques by Greg T. Hermanson, Academic Press, page 234-237). β-Gal contains abundant free sulfhydryl groups in its native state. The uptake of β-Gal provides a convenient read-out with the use of X-gal.

Briefly, 1 ml of $5 \times 10^{-3}$ M [Dmt¹]DALDA, [Phe¹]DALDA or [d-Arg-Dmt-Lys-Phe-NH$_2$] was mixed with 1 mg SMCC in phosphate buffer for 1 h at room temperature. This should result in "activated peptide." The "activated peptide" was diluted 1:10 with phosphate buffer. 1 mg of β-Gal was added to 1 ml of the 1:10 "activated peptide" and mixed at 4° C. for either 2 h or overnight.

Cells (N$_2$A neuroblastoma cells or Caco-2) were plated in 96-well plates ($2 \times 10^4$ cells/well) and incubated with β-Gal or β-Gal cross-linked with [Dmt¹]DALDA, [Phe¹]DALDA or [d-Arg-Dmt-Lys-Phe-NH$_2$] for 1 h at 37° C. Cells were then washed 4 times with phosphate buffer. The cells were then stained with β-gal staining set (Roche) for at least 2 h at 37° C. and examined under the microscope.

Figure 8:
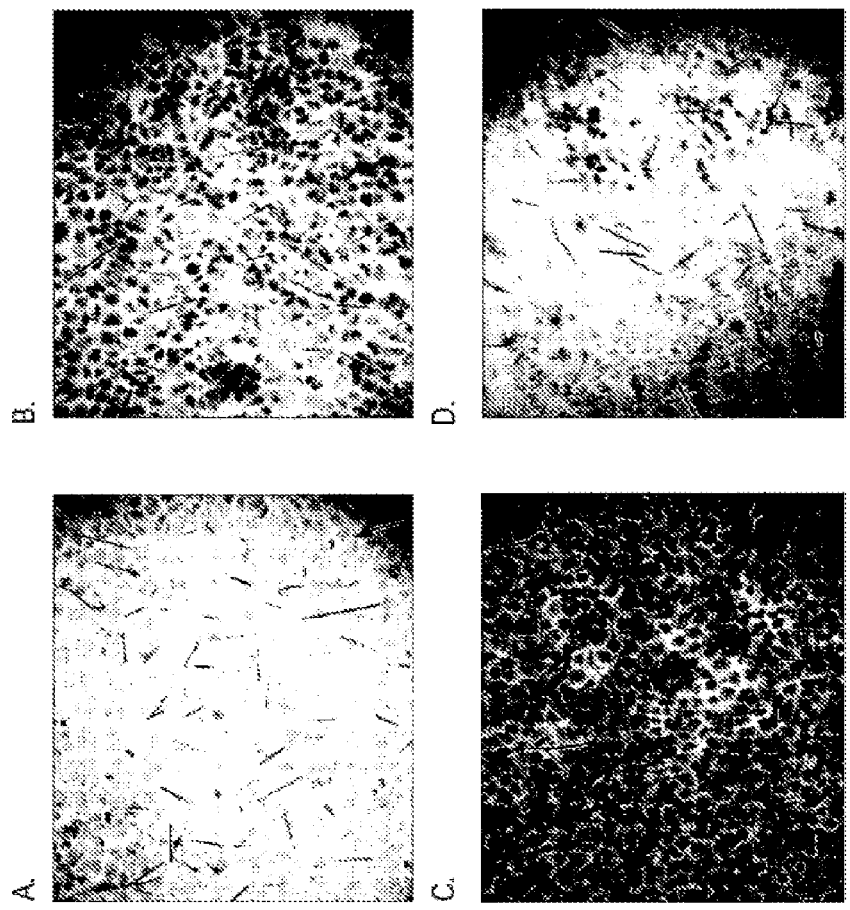
FIG. 8. Ability of peptides to enhance uptake of β-galactosidase (β-Gal) into N₂A neuroblastoma cells. Cells (N₂A neuroblastoma cells or Caco-2) were plated in 96-well plates (2×10⁴ cells/well) and incubated with β-Gal or β-Gal conjugated with peptide (via SMCC) for 1 h at 37° C. Cells were then washed 4 times with phosphate buffer. The cells were then stained with β-gal staining set (Roche) for at least 2 h at 37° C. and examined under the microscope. (A) no uptake of β-Gal was observed when Caco-2 cells were incubated with β-Gal. (B) presence of blue cells indicate uptake of β-Gal conjugated with [Dmt¹]DALDA in Caco-2 cells. (C) enhanced uptake of β-Gal conjugated with [D-Arg-Dmt-Lys-Phe-NH₂] in Caco-2 cells. (D) enhanced uptake of β-Gal conjugated with [Phe¹]DALDA in Caco-2 cells. Conjugation of β-Gal with SMCC alone did not enhance uptake.

No uptake of β-Gal was observed when Caco-2 cells were incubated with β-Gal (FIG. 8A). Presence of blue cells indicate uptake of β-Gal conjugated with [Dmt¹]DALDA in Caco-2 cells (FIG. 8B). Enhanced uptake of β-Gal was also found when it was conjugated with [d-Arg-Dmt-Lys-Phe-NH$_2$] (FIG. 8C) or [Phe¹]DALDA (FIG. 8D). Conjugation of β-Gal with SMCC alone did not enhance uptake.

Similar results were obtained when neuronal N$_2$A cells or CHO cells (Chinese hamster ovarian cells) were used.

Example 12: Co-Incubation with [Dmt¹]DALDA-SMCC Conjugate Enhances Uptake of Green Fluorescent Protein (GFP) into Huh7 Cells Huh7 cells ($1 \times 10^6$ cells/well) were washed with DMEM and then incubated with 0.5 ml DMEM containing 3 µg GFP alone, 3 µg GFP and 40 µl [Dmt¹]DALDA, or 3 µg GFP and 40 µl [Dmt¹]DALDA conjugated to SMCC for 60 min at 37° C. 2 ml of cell medium was then added to cells and incubated for an additional 24 hours in cell culture incubator. After incubation, cells were washed four times in cell medium and GFP retained in living cells was visualized by confocal laser scanning microscopy. Excitation was performed at 340 nm and emission was measured at 520 µM.

Figure 9:
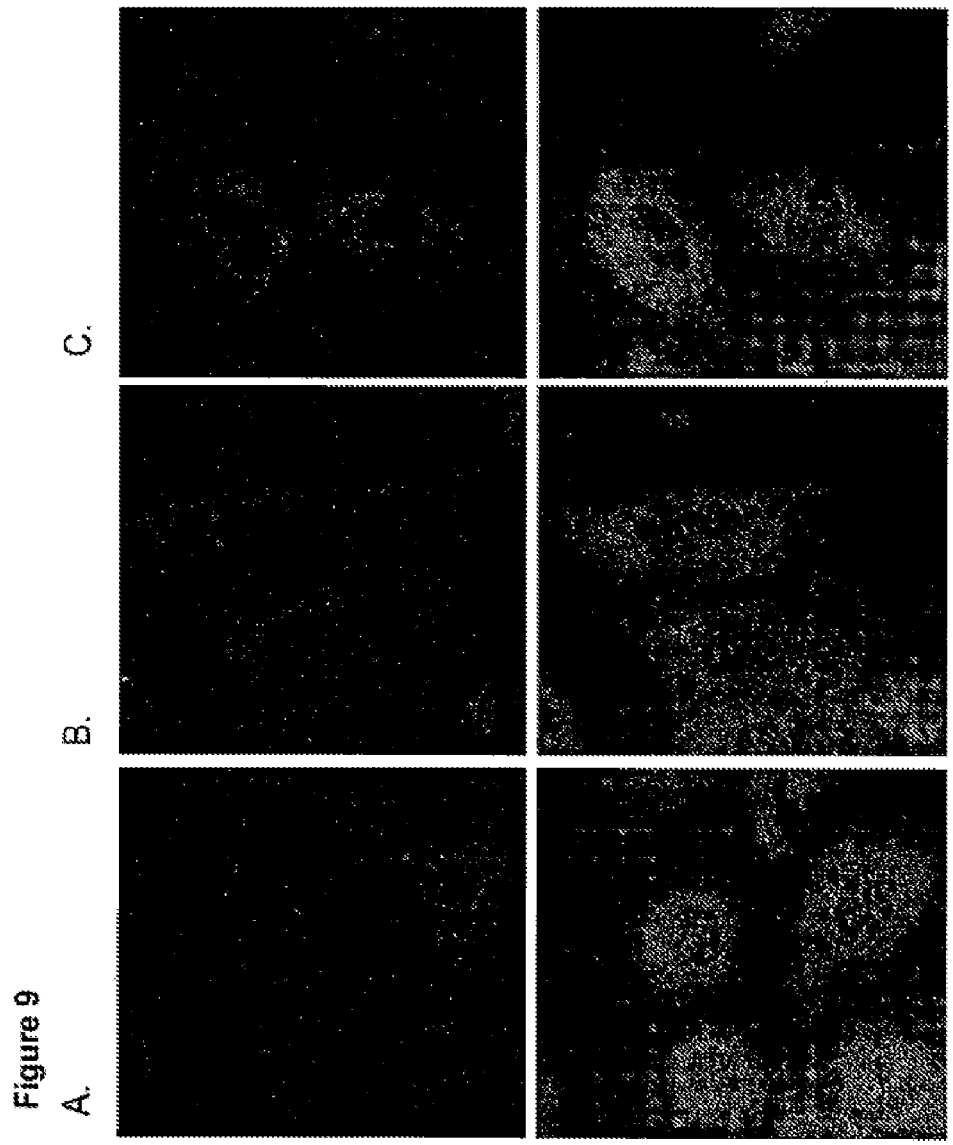
FIG. 9. Co-incubation with [Dmt¹]DALDA-SMCC conjugate enhances uptake of green fluorescent protein (GFP) into Huh7 cells. Huh7 cells (1×10⁶ cells/well) were washed with DMEM and then incubated with 0.5 ml DMEM containing 3 μg GFP alone (A), 3 μg GFP and 40 μl [Dmt¹] DALDA (B), or 3 μg GFP and 40 μl [Dmt¹]DALDA conjugated to SMCC(C) for 60 min at 37° C. 2 ml of cell medium was then added to cells and incubated for an additional 24 hours in cells incubator. After incubation, cells were washed four times in cell medium and GFP retained in living cells was visualized by confocal laser scanning microscopy. Excitation was performed at 340 nm and emission was measured at 520 nm. Top panel represents images of GFP through 0.8 μM thick central horizontal optical section of Huh7 cells. Bottom panel represents differential interface contrast images in same field.

FIG. 9 (top panel) represents images of GFP through 0.8 µM thick central horizontal optical section of Huh7 cells. FIG. 9 (bottom panel) represents differential interface contrast images in same field.

Co-incubation of GFP with [Dmt¹]DALDA showed moderately increased green fluorescence within the cell cytoplasm (FIG. 9B) compared to incubation with GFP alone (FIG. 9A). No green fluorescence was observed in the nucleus. Co-incubation of GFP with [Dmt¹]DALDA-SMCC conjugate showed even greater uptake of GFP (FIG. 9C). These data show that [Dmt¹]DALDA can promote protein uptake into cells by just physical mixing of the modified peptide with the protein, and that chemical conjugation between the peptide and the protein is not necessary.

Example 13: Conjugation of [Dmt]¹DALDA with an RNA Oligo

Figure 10:
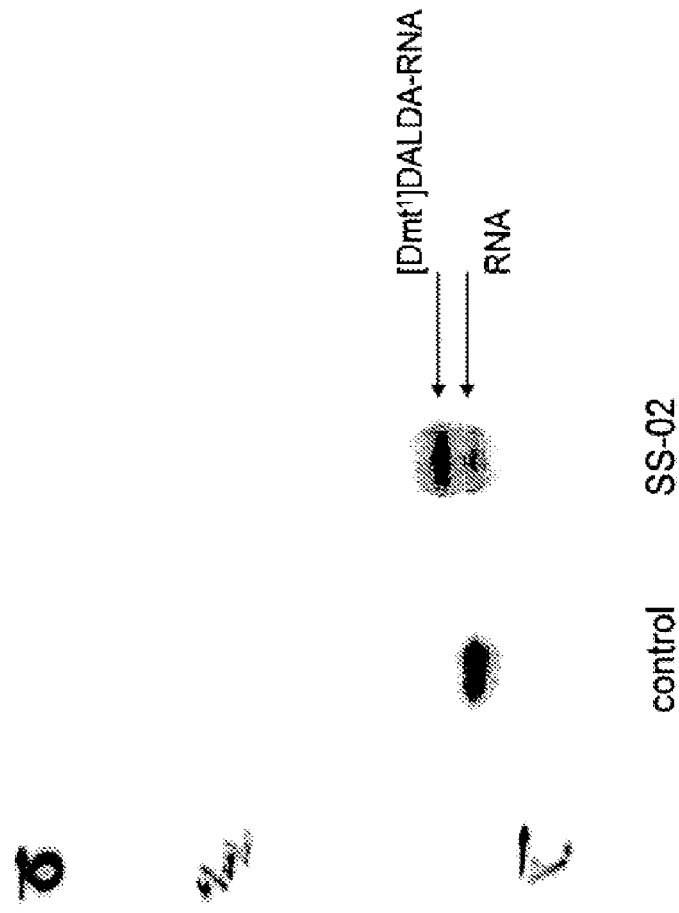
FIG. 10. Conjugation of [Dmt¹]DALDA with an RNA oligo. Synthetic RNA oligo (40 nucleotides long) was phosphorylated at the 5' end using γ-³²P-ATP and polynucleotide kinase. The product was purified by gel electrophoresis. 500,000 cpm of gel-purified RNA oligo was conjugated with [Dmt¹]DALDA in the presence of 1 mg EDC (N-[3-dimethylaminopropyl-N'-ethylcarboiimide]). The product of the conjugation reaction ([Dmt¹]DALDA-RNA oligo) and RNA oligo alone were analyzed on 15% polyacrylamide urea gel.

Synthetic RNA oligo (40 nucleotides long) was phosphorylated at the 5' end using γ-$^{32}$P-ATP in the reaction with polynucleotide kinase. The product was gel-purified for reaction. 500,000 counts per minute of gel-purified RNA oligo was conjugated in the reaction with 10 mM [Dmt]$^1$DALDA in the presence of 1 mg EDC (N-[3-dimethylaminopropyl-N'-ethylcarboiimide]). The product of conjugation reaction ([Dmt]'DALDA-RNA oligo) and control RNA oligo alone were analyzed on 15% polyacrylamide urea gel. Two distinct bands on the gel indicate the RNA oligo alone and the [Dmt$^1$]DALDA-RNA oligo conjugate (FIG. 10).

Example 14: Uptake of [Dmt]$^1$DALDA-RNA Oligo Conjugate into Caco-2 Cells

Caco-2 cells ($1\times10^6$) were washed three times in DMEM medium and preincubated in DMEM for 5 minutes before addition of oligos. Then, either [Dmt]$^1$DALDA-RNA oligo conjugate or unconjugated RNA (approximately 20,000 counts per minute each) were added to the cell medium and incubated for 60 min at 37° C.

After the incubation, reaction medium was removed and cells washed four times with DMEM and one time in sodium acetate solution to reduce nonspecific binding. Finally, the cells were incubated in lysis buffer for 30 minutes and radioactivity in the cell lysate was measured.

Figure 11:
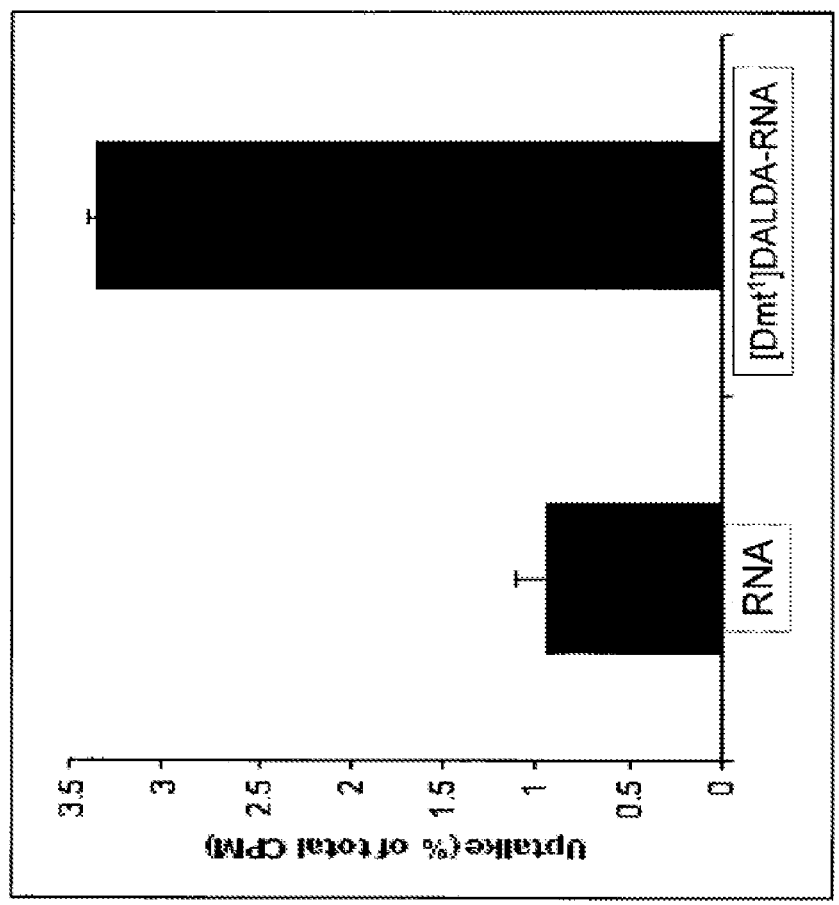
FIG. 11. Uptake of [Dmt¹]DALDA-[³²P]RNA oligo conjugate into Caco-2 cells. Caco-2 cells (1×10⁶) were washed three times in DMEM medium and preincubated in DMEM for 5 minutes. Cells were then incubated with [Dmt¹] DALDA-[³²P]RNA oligo conjugate or control RNA (approximately 20,000 cpm) for 60 minutes at 37° C. After incubation, the cells were washed, lysed, and radioactivity determined in the cell lysate. The uptake of [Dmt¹]DALDA-[³²P]RNA conjugate was >3-fold greater compared to RNA alone.

Caco-2 cells exhibited over three times greater uptake of [Dmt$^1$]DALDA-RNA oligo conjugate as compare to unconjugated RNA oligo alone (FIG. 11). Therefore, [Dmt]$^1$DALDA promotes passage of RNA oligo across the cell membrane.

Example 15: Mixing of RNA with [Dmt$^1$]DALDA-SMCC Linker Increases RNA Uptake into Cells The carrier complex was formed by physical mixing of RNA and [Dmt$^1$]DALDA-SMCC conjugate. The [Dmt$^1$]DALDA-SMCC conjugate was prepared by mixing [Dmt$^1$]DALDA with the cross-linker SMCC as described under Methods. A single strand 11-mer [$^{32}$P]RNA oligo was mixed with the [Dmt$^1$]DALDA-SMCC conjugate for 15 min at room temperature before use in cellular uptake studies.

Huh7 cells ($1\times10^6$ cells/well) were washed with DMEM and then incubated with 1.0 ml DMEM containing the [$^{32}$P]RNA oligo (100,000 cpm) alone or with 40 ml [Dmt$^1$]DALDA-SMCC conjugate at 37° C. or 4° C. Cells were then washed four times in DMEM and one time in sodium acetate solution to remove nonspecific binding before incubated in lysis buffer for 30 min and retained radioactivity determined.

Figure 12:
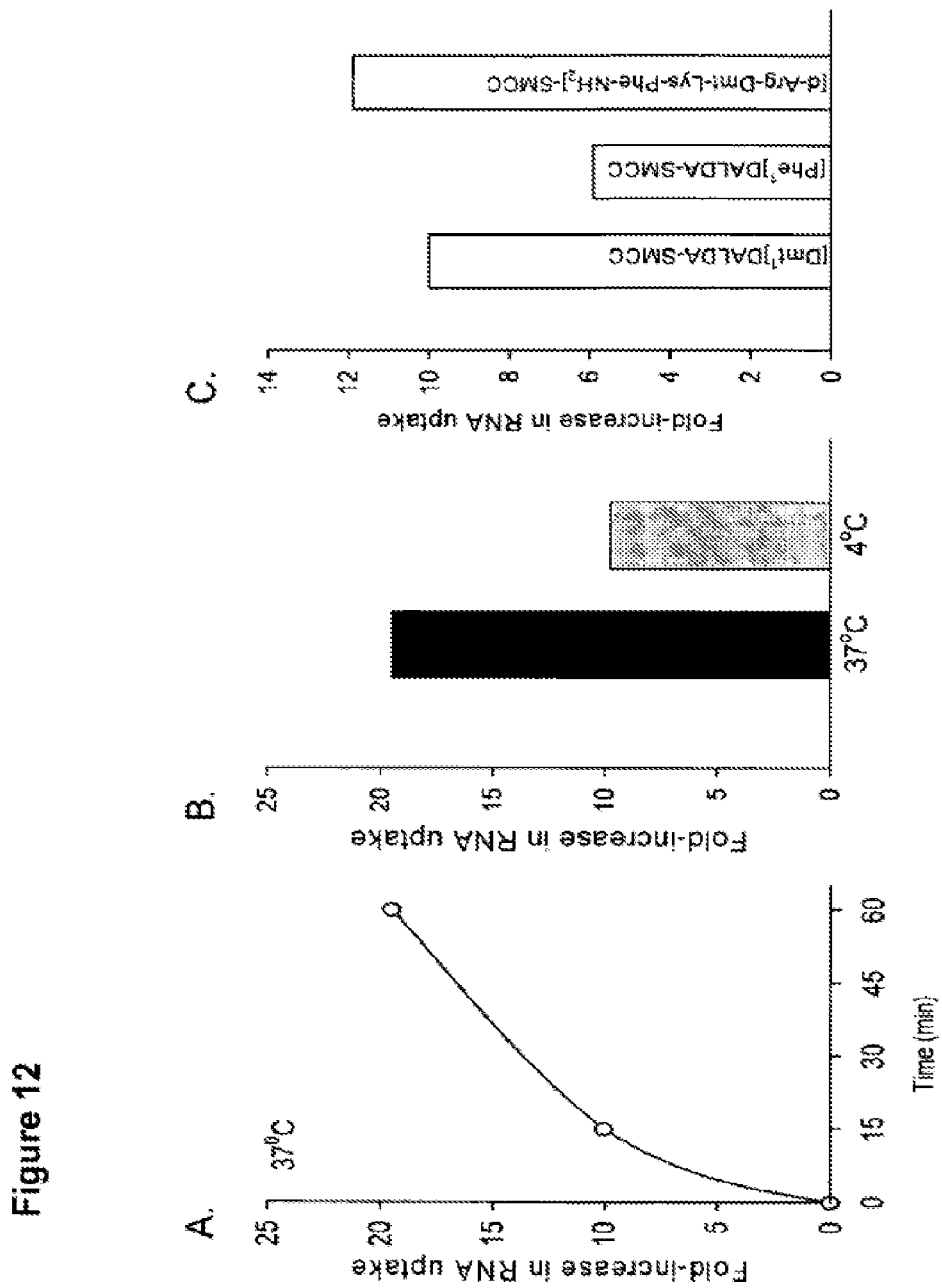
FIG. 12. Effect of peptide-SMCC conjugates to enhance uptake of RNA oligo into Huh7 cells. (A) Effect of time on cell uptake of RNA oligo. Huh7 cells (1×10⁶ cells/well) were washed with DMEM and then incubated with 1.0 ml DMEM containing [³²P]RNA oligo (single strand, 11 bases; ~100, 000 cpm) alone or with 40 ml [Dmt]DALDA-SMCC conjugate for 15 or 60 min at 37° C. Cells were then washed four times in DMEM and one time in sodium acetate solution to remove nonspecific binding before incubated in lysis buffer for 30 min and retained radioactivity determined. Co-incubation of RNA oligo with [Dmt¹]DALDA-SMCC at 37° C. increased uptake of the RNA oligo by 10-fold after 15 min incubation, and 20-fold after 60 min incubation. (B) Effect of temperature on cell uptake of RNA oligo. The ability of [Dmt¹]DALDA-SMCC to enhance RNA uptake was less at 4° C., although it was still increased uptake by 10-fold. (C). Enhanced cellular uptake of RNA by different peptide-SMCC conjugates. Huh7 cells ($1 \times 10^6$ cells/well) were washed with DMEM and then incubated with 1.0 ml DMEM containing [$^{32}$P]RNA oligo alone or with 40 ml peptide-SMCC conjugate for 15 minutes at 37° C. All three peptide-SMCC conjugates increased RNA uptake.

Co-incubation of RNA oligo with [Dmt$^1$]DALDA-SMCC at 37° C. increased uptake of the RNA oligo as a function of time (FIG. 12A). At one hour, the uptake of RNA oligo in the presence of [Dmt$^1$]DALDA-SMCC was increased ~20-fold compared to incubation with RNA alone. The uptake of RNA was significantly enhanced by [Dmt$^1$]DALDA-SMCC even at 4° C. (FIG. 12B). These data show that it is possible to enhance RNA uptake without chemical conjugation with [Dmt$^1$]DALDA. The uptake at 4° C. indicates uptake by energy-independent non-endocytotic processes, consistent with the ability of [Dmt$^1$]DALDA to penetrate cell membranes by passive diffusion.

In addition to [Dmt$^1$]DALDA-SMCC, co-incubation with [Phe$^1$]DALDA-SMCC or [d-Arg-Dmt-Lys-Phe-NH$_2$]-SMCC also enhanced the uptake of the 11-mer RNA oligo. FIG. 12C shows the increase in RNA uptake when incubated with the three different peptide-SMCC conjugates for 15 min at 37° C.

Figure 13:
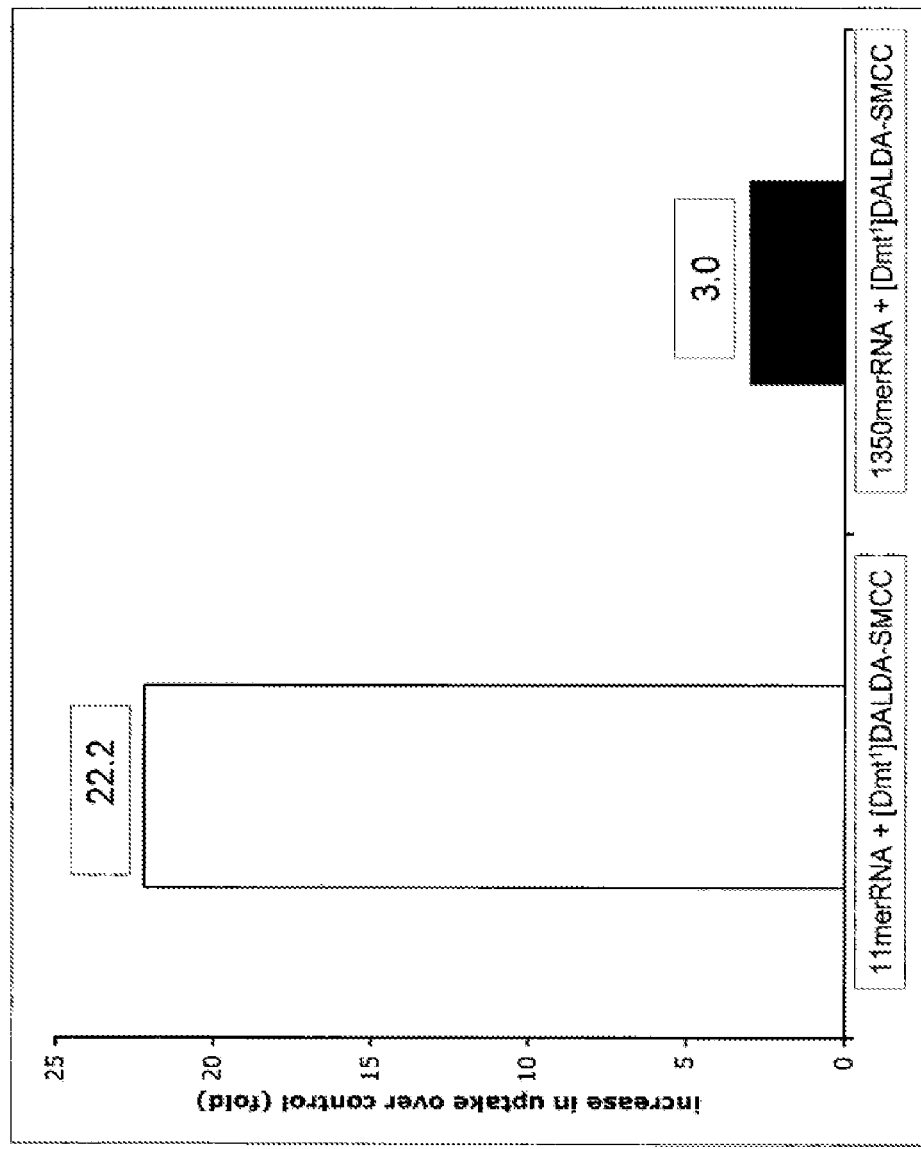
FIG. 13. Co-incubation with [Dmt¹]DALDA-SMCC conjugate enhanced uptake of two RNAs of different lengths. [Dmt¹]DALDA was conjugated with SMCC and confirmed by mass spectroscopy. An 11-mer RNA oligo and a 1350-mer RNA were mixed with the [Dmt¹]DALDA-SMCC conjugate for 15 min at room temperature. Huh7 cells ($1 \times 10^6$ cells/well) were washed with DMEM and then incubated with 1 ml DMEM containing either the RNA alone (~100,000 cpm), or the RNA mixed with the [Dmt¹]DALDA-SMCC conjugate for 60 min at 37° C. and 5% $CO_2$. The cells were then washed four times in DMEM and one time in sodium acetate solution to remove nonspecific binding. The washed cells were then incubated in lysis buffer for 30 min and retained radioactivity counted. Compared to incubation with RNA alone, co-incubation with the [Dmt¹]DALDA-SMCC conjugate increased the uptake of the 11-mer RNA by 22-fold, and the uptake of the 1350-mer RNA by 3-fold.

Co-incubation with [Dmt$^1$]DALDA-SMCC conjugate can also promote the cellular uptake of a much larger RNA molecule (1350-mer) as shown in FIG. 13, although not as much as for a smaller oligo.

Example 16: Conjugation of [Dmt$^1$]DALDA with a DNA Olio

SMCC (1 µg) and [Dmt$^1$]DALDA (SS002; 5 µg) were dissolved together in 2 ml of PBS, incubated at room temperature for 30 min, and mixed with deprotected 3'-thiol DNA oligo at 4° C. for 24 hours. After incubation, an aliquot of sample was mixed with matrix (saturated 3-hydroxy picolinic acid (HPA) in 50% acetonitrile, 10 mg/ml ammonium citrate) in a 1:10 ratio, and spotted on a stainless steel target plate.

Figure 14:
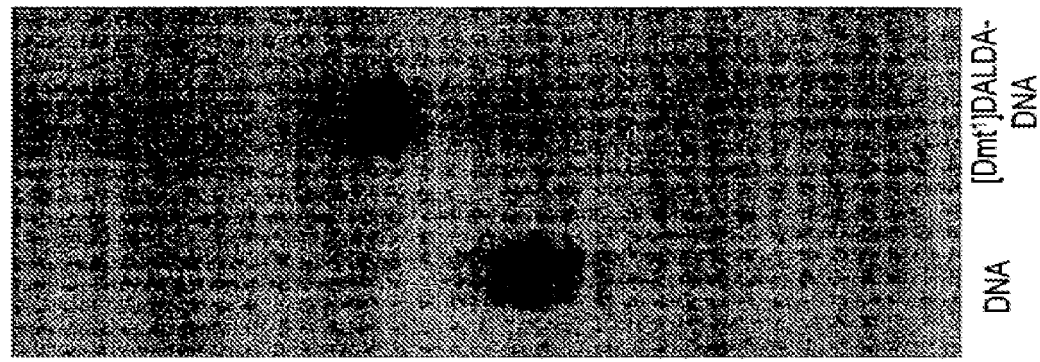
FIG. 14. Conjugation of DNA oligo to [Dmt¹]DALDA. SMCC (1 µg) and [Dmt¹]DALDA (5 µg) were dissolved together in 2 ml of PBS, incubated at room temperature for 30 min, and mixed with deprotected 3'-thiol DNA oligo at 4° C. for 24 hours. After incubation, an aliquot of sample was mixed with matrix (saturated 3-hydroxy picolinic acid (HPA) in 50% acetonitrile, 10 mg/ml ammonium citrate) in a 1:10 ratio, and spotted on a stainless steel target plate. Samples were analyzed by MALDI-TOF MS (A). The molecular weights of 3'-thiol DNA oligo and [Dmt¹]DALDA-DNA covalent complex were found to be 6392 and 7171, respectively. Both conjugated and unconjugated oligos were phosphorylated at the 5'-end using $\gamma$-$^{32}$P-ATP in the reaction with polynucleotide kinase, and the products of kinase reaction were analyzed on 15% polyacrylamide urea gel and gel-purified for cellular uptake studies (B).
Figure 14:
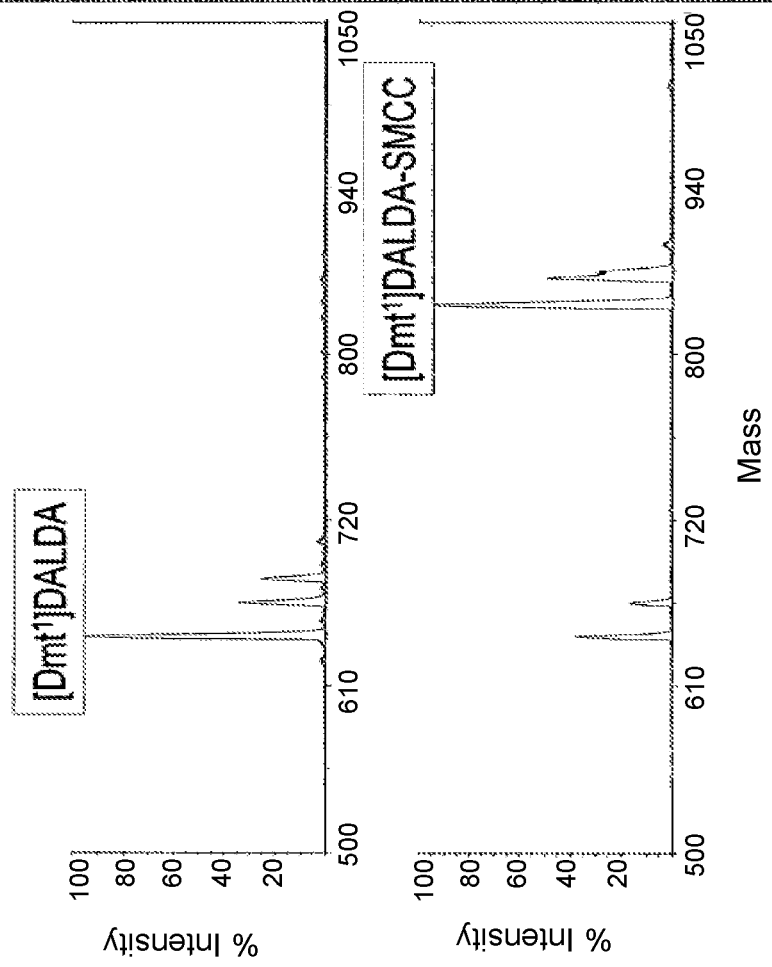

The formation of the DNA-[Dmt$^1$]DALDA conjugate was confirmed by MALDI-TOF MS. The molecular weights of 3'-thiol DNA oligo and [Dmt$^1$]DALDA-DNA covalent complex were found to be 6392 and 7171, respectively (FIG. 14A).

Example 17: Uptake of [Dmt]$^1$DALDA-DNA Oligo Conjugate into Caco-2 Cells

A 3'-thiol-modified 20-mer DNA was conjugated to [Dmt$^1$]DALDA using SMCC, and the formation of the conjugate was confirmed by mass spectroscopy. Both conjugated and unconjugated DNA oligos were radiolabeled at the 5'-end with $^{32}$P and gel-purified (FIG. 14B)

Neuronal N$_2$A ($1\times10^6$ cells/well) cells were washed with DMEM and incubated with 1 ml DMEM containing either [Dmt$^1$]DALDA-conjugated or unconjugated DNA oligo (~100,000 dpm) for 2 h or 19 h at 37° C. and 5% CO$_2$. Cells were then washed four times in DMEM and one time in sodium acetate solution to reduce nonspecific binding. The cells were then incubated in lysis buffer for 30 min and retained radioactivity determined.

Figure 15:
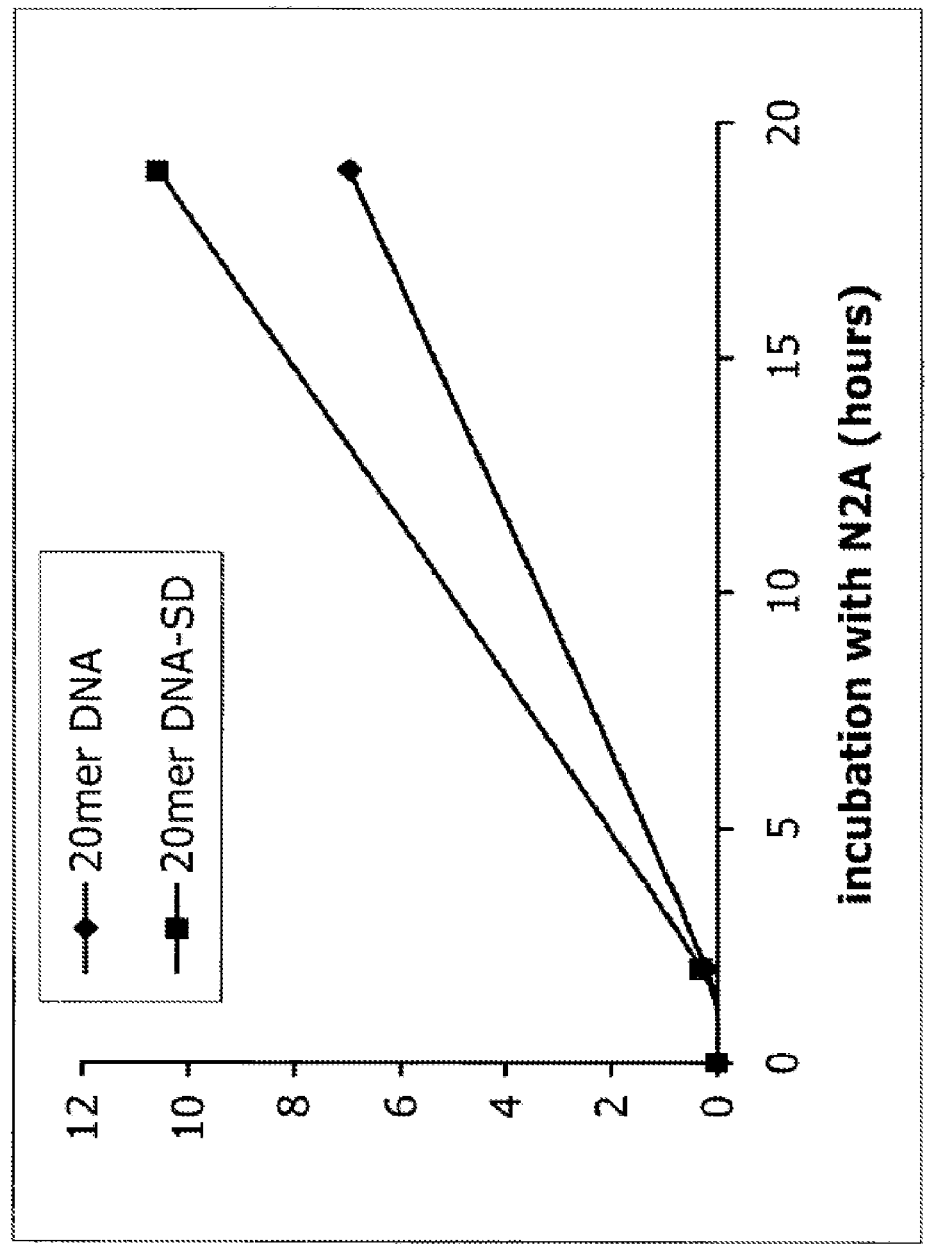
FIG. 15. Cellular uptake of DNA oligo conjugated with [Dmt¹]DALDA. A 3'-thiol-modified 20-mer DNA was conjugated to [Dmt¹]DALDA using SMCC, and the formation of the conjugate was confirmed by mass spectroscopy. Both conjugated and unconjugated DNA oligos were radiolabeled at the 5'-end with $^{32}$P and gel-purified. Neuronal $N_2A$ ($1 \times 10^6$ cells/well) cells were washed with DMEM and incubated with 1 ml DMEM containing either [Dmt¹]DALDA-conjugated or unconjugated DNA oligo (~100,000 cpm) for 2 h or 19 h at 37° C. and 5% $CO_2$. Cells were then washed four times in DMEM and one time in sodium acetate solution to remove nonspecific binding. The cells were then incubated in lysis buffer for 30 min and retained radioactivity determined. Y-axis shows uptake of DNA represented as percent of total radioactivity.

Uptake of DNA conjugated with [Dmt$^1$]DALDA was greater compared to unconjugated DNA after 19 h of incubation (FIG. 15), indicating that DNA uptake can be enhanced by conjugation to [Dmt$^1$]DALDA.

Example 18: Peptides and Peptide-SMCC Conjugates are not Toxic to Cells

Figure 16:
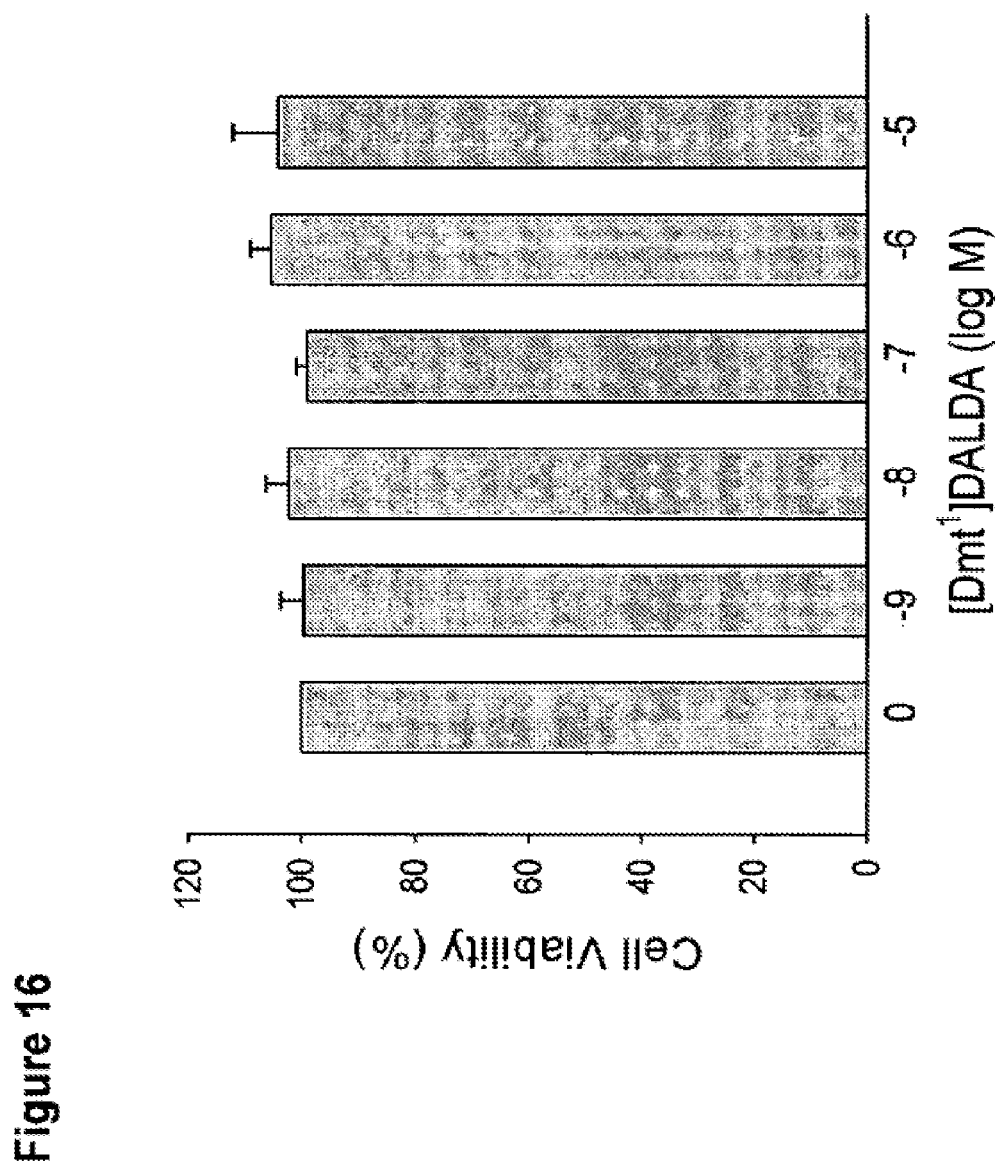
FIG. 16. [Dmt¹]DALDA is not toxic to cells in culture. Neuronal $N_2$ cells were incubated with [Dmt¹]DALDA (1 nM to 10 µM) for 24 h and cell viability was determined by the MTT assay.

Neither the peptides nor the peptide-SMCC conjugates are toxic to cells in culture. Treatment with [Dmt$^1$]DALDA (1 nM to 10 µM) for 24 h had no effect on cell viability as measured by the MTT assay (MTS assay, Promega, Madison, Wis.) in N$_2$A cells (FIG. 16), SH-SY5Y cells or Caco-2 cells. Similar studies with [D-Arg-Dmt-Lys-Phe-NH$_2$) also showed no effect on cell viability.

Incubation of cells in culture with the peptide-SMCC conjugates also did not affect cell viability as measured by the uptake of trypan blue. Trypan blue is only taken by cells with increased membrane permeability. Huh7 cells ($1\times10^6$) were washed three times in DMEM, and 1 ml of fresh medium, or media containing 50 ml of 1 mM [Dmt$^1$]DALDA-SMCC conjugate, [D-Arg-Dmt-Lys-Phe-NH$_2$]-SMCC conjugate, or [Phe$^1$]DALDA-SMCC conjugate, and incubated at 37° C. for 24 hours at 5% CO$_2$. Cells were then washed three times with DMEM, and 1 ml of 0.4% trypan blue was added to the cells for 2 minutes. Excessive dye was removed by washing cells in cell medium and the cells were examined by light microscopy.

Examination of cells by light microscopy demonstrated that cells incubated with media alone showed minimal trypan blue uptake. No increase in trypan blue uptake was observed in cells incubated with [Dmt¹]DALDA-SMCC, [D-Arg-Dmt-Lys-Phe-NH₂]-SMCC, or [Phe¹]DALDA. In contrast, incubation of cells with DEPC (diethylpyrocarbonate) resulted in significant uptake of trypan blue.

Figure 17:
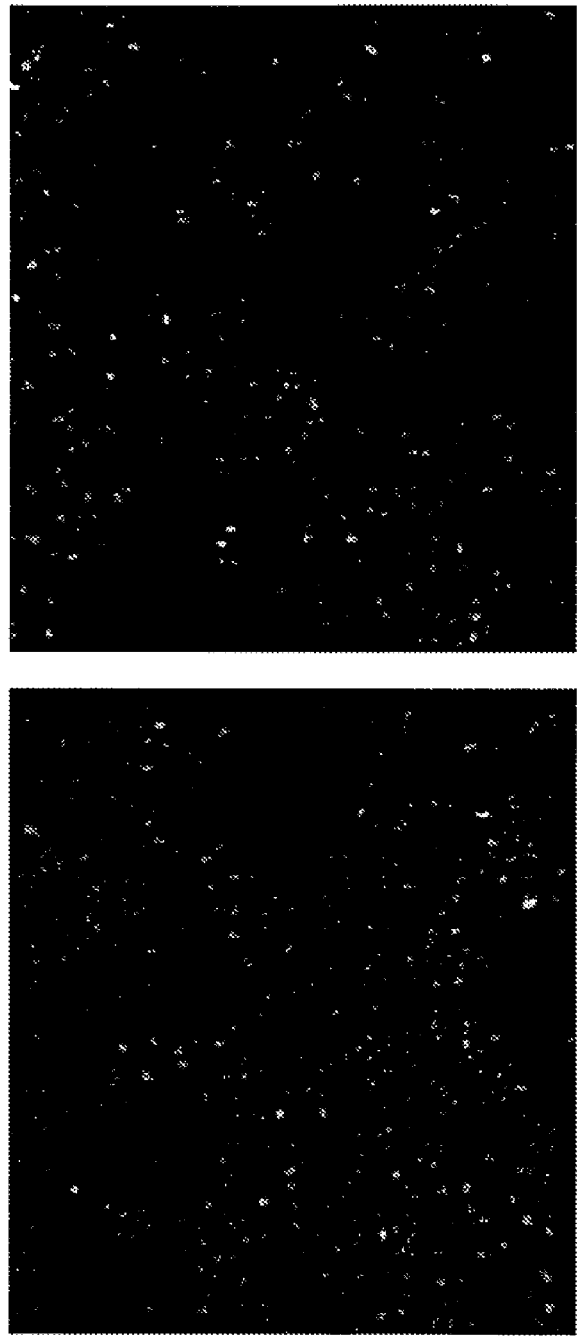
FIG. 17. [Dmt¹]DALDA-SMCC conjugate does not induce apoptosis in Huh7 cells. Huh7 cells ($1 \times 10^6$ cells/well) were washed three times in DMEM, and 1 ml of fresh medium was applied. Then, either 50 µl of [Dmt¹]DALDA-SMCC conjugate (1 mM) in PBS or PBS only (control) was added to the cell medium and incubated at 37° C. for 24 hours at 5% $CO_2$. After incubation, 1 µl of Hoechst dye for staining apoptotic nuclei was added to the cells and incubated for an additional 15 min. Excessive Hoechst dye was removed by washing cells with cell medium (free of pH indicator) and cells treated with [Dmt¹]DALDA-SMCC conjugate were compared with control cells using fluorescent microscopy (excitation at 350 nm and emission at 461 nm).

Incubation of cells in culture with [Dmt¹]DALDA-SMCC conjugate also did not induce apoptosis in Huh7 cells in culture. Huh7 cells ($1\times10^6$ cells/well) were washed three times in DMEM, and 1 ml of fresh medium was applied. Then, either 50 μl of modified [Dmt¹]DALDA (1 mM) in PBS or PBS only (control) were added to the cell medium and incubated at 37° C. for 24 hours at 5% $CO_2$. After the incubation, 1 ml of Hoechst dye (Molecular Probes, Eugene, Oreg.) for staining apoptotic nuclei were added to cells and incubated for additional 15 min. Excessive Hoechst dye was removed by washing cells with cell medium (free of pH indicator) and cells treated with [Dmt¹]DALDA-SMCC conjugate were compared with control cells using fluorescent microscopy (excitation at 350 nm and emission at 461 μM). Apoptosis is indicated by concentration of fluorescence in the nuclei. FIG. 17 demonstrates that the level of apoptosis in Huh7 cells treated with [Dmt]DALDA-SMCC is the same as in control cells.

---

What is claimed is:

1. A carrier complex comprising a molecule conjugated to an aromatic cationic peptide, wherein the aromatic cationic peptide is selected from the group consisting of:
   Phe-D-Arg-Phe-Lys-NH$_2$ (Phe$^1$-DALDA),
   D-Arg-2',6'-Dmt-Lys-Phe-NH$_2$, and
   2',6'-Dmp-D-Arg-Phe-Lys-NH$_2$ (Dmp$^1$-DALDA),
   and wherein the molecule is a lipid, an enzyme, an antibody, or a neurotrophic growth factor.

2. The carrier complex according to claim 1, wherein the molecule is conjugated to the aromatic cationic peptide by a linker.

3. The carrier complex according to claim 2, wherein the linker is a component of the aromatic-cationic peptide.

4. The carrier complex according to claim 2, wherein the linker is a component of the molecule.

5. The carrier complex according to claim 1, wherein the molecule and aromatic cationic peptide are chemically bonded.

6. The carrier complex according to claim 1, wherein the molecule and aromatic cationic peptide are physically bonded.

7. A method for delivering a molecule to a cell, the method comprising contacting the cell with a carrier complex, wherein the carrier complex comprises the molecule conjugated to an aromatic cationic peptide, wherein the aromatic cationic peptide is selected from the group consisting of:
   Phe-D-Arg-Phe-Lys-NH$_2$ (Phe$^1$-DALDA),
   D-Arg-2',6'-Dmt-Lys-Phe-NH$_2$, and
   2',6'-Dmp-D-Arg-Phe-Lys-NH$_2$ (Dmp$^1$-DALDA);
   and wherein the molecule is a lipid, an enzyme, an antibody, or a neurotrophic growth factor.

8. The method according to claim 7, wherein the molecule is conjugated to the aromatic cationic peptide by a linker.

9. The method according to claim 8, wherein the linker is a component of the aromatic-cationic peptide.

10. The method according to claim 8, wherein the linker is a component of the molecule.

11. The method according to claim 7, wherein the molecule and aromatic cationic peptide are chemically bonded.

12. The method according to claim 7, wherein the molecule and aromatic cationic peptide are physically bonded.

* * * * *